(12) United States Patent
Akao

(10) Patent No.: US 10,874,688 B2
(45) Date of Patent: Dec. 29, 2020

(54) DOUBLE-STRANDED NUCLEIC ACID MOLECULE AND USE THEREOF

(71) Applicant: GIFU UNIVERSITY, Gifu (JP)

(72) Inventor: Yukihiro Akao, Gifu (JP)

(73) Assignee: GIFU UNIVERSITY, Gifu (JP)

( * ) Notice: Subject to any disclaimer, the term of this patent is extended or adjusted under 35 U.S.C. 154(b) by 0 days.

(21) Appl. No.: 16/345,296

(22) PCT Filed: Oct. 31, 2017

(86) PCT No.: PCT/JP2017/039364
§ 371 (c)(1),
(2) Date: Apr. 26, 2019

(87) PCT Pub. No.: WO2018/079841
PCT Pub. Date: May 3, 2018

(65) Prior Publication Data
US 2019/0262378 A1    Aug. 29, 2019

(30) Foreign Application Priority Data

Oct. 31, 2016 (JP) ................................ 2016-213131

(51) Int. Cl.
| | |
|---|---|
| *A61K 31/713* | (2006.01) |
| *A61P 35/02* | (2006.01) |
| *C12N 15/113* | (2010.01) |
| *C12N 15/85* | (2006.01) |
| *A61K 48/00* | (2006.01) |
| *A61P 35/00* | (2006.01) |
| *C12N 15/09* | (2006.01) |

(52) U.S. Cl.
CPC ............ *A61K 31/713* (2013.01); *A61K 48/00* (2013.01); *A61P 35/00* (2018.01); *A61P 35/02* (2018.01); *C12N 15/09* (2013.01); *C12N 15/1135* (2013.01); *C12N 15/85* (2013.01)

(58) Field of Classification Search
CPC ....... A61K 31/713; A61K 48/00; A61P 35/00; A61P 35/02; C12N 15/09
USPC ..................... 435/6.1, 91.1, 91.31, 455, 458; 514/44 A; 536/23.1, 24.5
See application file for complete search history.

(56) References Cited

FOREIGN PATENT DOCUMENTS

| | | | |
|---|---|---|---|
| JP | 2008-519606 A | 6/2008 | |
| WO | 2007/094135 A1 | 8/2007 | |
| WO | WO-2007094135 A1 * | 8/2007 | ............ C07F 9/6512 |
| WO | 2010/032704 A1 | 3/2010 | |
| WO | WO-2010032704 A1 * | 3/2010 | ................ A61P 1/00 |
| WO | 2012177639 A2 | 12/2012 | |
| WO | 2013/162041 A1 | 10/2013 | |
| WO | 2017/179660 A1 | 10/2017 | |
| WO | WO-2017179660 A1 * | 10/2017 | ........... A61K 31/713 |

OTHER PUBLICATIONS

Cui et al, J. Cell Mol. Med., vol. 18, No. 10, pp. 1913-1926. (Year: 2014).*
International Search Report dated Feb. 20, 2018 for PCT/2017/039364 and English translation.
Shi-Yun Cui et al., Journal of Cellular and Molecular Medicine (2014) 18, 1913-1926.
MS Ostenfeld et al., Oncogene (2010) 29, 1073-1084.
Lea H. Gregersen et al., Plos One (2010) 5, e8836.
Daniel T. Starczynowski et al., Blood (2011) 117, 595-607.
MS Zaman et al., British Journal of Cancer (2010) 103, 256-264.
Shihua Wang et al., International Journal of Oncology (2009) 34, 1461-1466.
Shi-Bin Jiang et al., OncoTargets and Therapy (2016) 2016, 2305-2315.
Sheema Khan et al., Oncotarget (2016) 5, 7599-7609.
Steiner, F. A. et al., Structural features of small RNA ... 2007,14(10),p. 927-933.
EPO, Extended European Search Report for the corresponding European patent application No. 17865295.4, dated Aug. 11, 2019 (10 pages).
Sequence ID No. 1762547 from PCT application publication No. WO2012177639A2, dated Dec. 27, 2012.

* cited by examiner

*Primary Examiner* — Jane J Zara
(74) *Attorney, Agent, or Firm* — Lucas & Mercanti, LLP

(57) ABSTRACT

A double-stranded nucleic acid molecule includes a first polynucleotide chain including a base sequence represented by Chemical Formula (1) (SEQ ID NO:1) and a second polynucleotide chain including a base sequence complementary to the first polynucleotide chain. A method for preventing and/or treating a tumor includes a step in which the double-stranded nucleic acid molecule is administered to a test subject.

15 Claims, 6 Drawing Sheets

Specification includes a Sequence Listing.

SEQUENCE LISTING

```
<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Combined DNA/RNA molecule
<220> FEATURE:
<221> NAME/KEY: misc_feature
<222> LOCATION: (6)..(7)
<223> OTHER INFORMATION: n is t or u
<220> FEATURE:
```

```
<221> NAME/KEY: misc_feature
<222> LOCATION: (10)..(10)
<223> OTHER INFORMATION: n is t or u
<220> FEATURE:
<221> NAME/KEY: misc_feature
<222> LOCATION: (19)..(19)
<223> OTHER INFORMATION: n is t or u
<220> FEATURE:
<221> NAME/KEY: misc_feature
<222> LOCATION: (24)..(25)
<223> OTHER INFORMATION: n is a, c, g, t, u or deletion

<400> SEQUENCE: 1
agggannccn gggaaaacng gacnn                                              25

<210> SEQ ID NO 2
<211> LENGTH: 25
<212> TYPE: DNA
<213> ORGANISM: Artificial Sequence
<220> FEATURE:
<223> OTHER INFORMATION: Combined DNA/RNA molecule
<220> FEATURE:
<221> NAME/KEY: misc_feature
<222> LOCATION: (24)..(25)
<223> OTHER INFORMATION: n is a, c, g, t, u or deletion

<400> SEQUENCE: 2
guccaguuuu cccaggaauc ccunn                                              25

<210> SEQ ID NO 3
<211> LENGTH: 25
<212> TYPE: RNA
<213> ORGANISM: Artificial Sequence
<220> FEATURE:
<223> OTHER INFORMATION: Polynucleotide

<400> SEQUENCE: 3
agggauuccu gggaaaacug gacgg                                              25

<210> SEQ ID NO 4
<211> LENGTH: 25
<212> TYPE: RNA
<213> ORGANISM: Artificial Sequence
<220> FEATURE:
<223> OTHER INFORMATION: Polynucleotide

<400> SEQUENCE: 4
guccaguuuu cccaggaauc ccugg                                              25

<210> SEQ ID NO 5
<211> LENGTH: 25
<212> TYPE: DNA
<213> ORGANISM: Artificial Sequence
<220> FEATURE:
<223> OTHER INFORMATION: Combined DNA/RNA molecule

<400> SEQUENCE: 5
guccaguuuu cccaggaauc ccutt                                              25

<210> SEQ ID NO 6
<211> LENGTH: 25
<212> TYPE: DNA
<213> ORGANISM: Artificial Sequence
<220> FEATURE:
<223> OTHER INFORMATION: Combined DNA/RNA molecule

<400> SEQUENCE: 6
agggauuccu gggaaaacug gactt                                              25
```

-continued

```
<210> SEQ ID NO 7
<211> LENGTH: 22
<212> TYPE: RNA
<213> ORGANISM: Homo sapiens

<400> SEQUENCE: 7
ggauuccugg aaauacuguu cu                                                  22

<210> SEQ ID NO 8
<211> LENGTH: 23
<212> TYPE: RNA
<213> ORGANISM: Homo sapiens

<400> SEQUENCE: 8
guccaguuuu cccaggaauc ccu                                                 23

<210> SEQ ID NO 9
<211> LENGTH: 25
<212> TYPE: DNA
<213> ORGANISM: Artificial Sequence
<220> FEATURE:
<223> OTHER INFORMATION: Combined DNA/RNA molecule
<220> FEATURE:
<221> NAME/KEY: misc_feature
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: um
<220> FEATURE:
<221> NAME/KEY: misc_feature
<222> LOCATION: (3)..(3)
<223> OTHER INFORMATION: 2'-fluorocytidine
<220> FEATURE:
<221> NAME/KEY: modified_base
<222> LOCATION: (4)..(4)
<223> OTHER INFORMATION: cm
<220> FEATURE:
<221> NAME/KEY: misc_feature
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: gm
<220> FEATURE:
<221> NAME/KEY: misc_feature
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: um
<220> FEATURE:
<221> NAME/KEY: misc_feature
<222> LOCATION: (9)..(9)
<223> OTHER INFORMATION: 2'-fluorouridine
<220> FEATURE:
<221> NAME/KEY: modified_base
<222> LOCATION: (10)..(10)
<223> OTHER INFORMATION: um
<220> FEATURE:
<221> NAME/KEY: misc_feature
<222> LOCATION: (11)..(11)
<223> OTHER INFORMATION: 2'-fluorocytidine
<220> FEATURE:
<221> NAME/KEY: modified_base
<222> LOCATION: (12)..(12)
<223> OTHER INFORMATION: cm
<220> FEATURE:
<221> NAME/KEY: misc_feature
<222> LOCATION: (13)..(13)
```

```
<223> OTHER INFORMATION: 2'-fluorocytidine
<220> FEATURE:
<221> NAME/KEY: misc_feature
<222> LOCATION: (14)..(14)
<223> OTHER INFORMATION: 2'-O-methyladenosine
<220> FEATURE:
<221> NAME/KEY: misc_feature
<222> LOCATION: (15)..(15)
<223> OTHER INFORMATION: 2'-fluoroguanosine
<220> FEATURE:
<221> NAME/KEY: modified_base
<222> LOCATION: (16)..(16)
<223> OTHER INFORMATION: gm
<220> FEATURE:
<221> NAME/KEY: misc_feature
<222> LOCATION: (17)..(17)
<223> OTHER INFORMATION: 2'-fluoroadenosine
<220> FEATURE:
<221> NAME/KEY: misc_feature
<222> LOCATION: (18)..(18)
<223> OTHER INFORMATION: 2'-O-methyladenosine
<220> FEATURE:
<221> NAME/KEY: misc_feature
<222> LOCATION: (19)..(19)
<223> OTHER INFORMATION: 2'-fluorouridine
<220> FEATURE:
<221> NAME/KEY: modified_base
<222> LOCATION: (20)..(20)
<223> OTHER INFORMATION: cm
<220> FEATURE:
<221> NAME/KEY: misc_feature
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: cm
<220> FEATURE:
<221> NAME/KEY: misc_feature
<222> LOCATION: (23)..(23)
<223> OTHER INFORMATION: 2'-fluorouridine
<220> FEATURE:
<221> NAME/KEY: misc_feature
<222> LOCATION: (24)..(24)
<223> OTHER INFORMATION: 2'-O-methylthymidine
<220> FEATURE:
<221> NAME/KEY: misc_feature
<222> LOCATION: (25)..(25)
<223> OTHER INFORMATION: 2'-fluorothymidine

<400> SEQUENCE: 9
guccaguuuu cccaggaauc ccutt                                          25

<210> SEQ ID NO 10
<211> LENGTH: 25
<212> TYPE: DNA
<213> ORGANISM: Artificial Sequence
<220> FEATURE:
<223> OTHER INFORMATION: Combined DNA/RNA molecule
<220> FEATURE:
<221> NAME/KEY: misc_feature
<222> LOCATION: (1)..(1)
<223> OTHER INFORMATION: 2'-fluoroadenosine
<220> FEATURE:
<221> NAME/KEY: modified_base
<222> LOCATION: (2)..(2)
<223> OTHER INFORMATION: gm
<220> FEATURE:
<221> NAME/KEY: misc_feature
<222> LOCATION: (3)..(3)
<223> OTHER INFORMATION: 2'-fluoroguanosine
<220> FEATURE:
<221> NAME/KEY: modified_base
<222> LOCATION: (4)..(4)
<223> OTHER INFORMATION: gm
<220> FEATURE:
<221> NAME/KEY: misc_feature
```

```
<222> LOCATION: (5)..(5)
<223> OTHER INFORMATION: 2'-fluoroadenosine
<220> FEATURE:
<221> NAME/KEY: modified_base
<222> LOCATION: (6)..(6)
<223> OTHER INFORMATION: um
<220> FEATURE:
<221> NAME/KEY: misc_feature
<222> LOCATION: (7)..(7)
<223> OTHER INFORMATION: 2'-fluorouridine
<220> FEATURE:
<221> NAME/KEY: modified_base
<222> LOCATION: (8)..(8)
<223> OTHER INFORMATION: cm
<220> FEATURE:
<221> NAME/KEY: misc_feature
<222> LOCATION: (9)..(9)
<223> OTHER INFORMATION: 2'-fluorocytidine
<220> FEATURE:
<221> NAME/KEY: modified_base
<222> LOCATION: (10)..(10)
<223> OTHER INFORMATION: um
<220> FEATURE:
<221> NAME/KEY: misc_feature
<222> LOCATION: (11)..(11)
<223> OTHER INFORMATION: 2'-fluoroguanosine
<220> FEATURE:
<221> NAME/KEY: modified_base
<222> LOCATION: (12)..(12)
<223> OTHER INFORMATION: gm
<220> FEATURE:
<221> NAME/KEY: misc_feature
<222> LOCATION: (13)..(13)
<223> OTHER INFORMATION: 2'-fluoroguanosine
<220> FEATURE:
<221> NAME/KEY: misc_feature
<222> LOCATION: (14)..(14)
<223> OTHER INFORMATION: 2'-O-methyladenosine
<220> FEATURE:
<221> NAME/KEY: misc_feature
<222> LOCATION: (15)..(15)
<223> OTHER INFORMATION: 2'-fluoroadenosine
<220> FEATURE:
<221> NAME/KEY: misc_feature
<222> LOCATION: (16)..(16)
<223> OTHER INFORMATION: 2'-O-methyladenosine
<220> FEATURE:
<221> NAME/KEY: misc_feature
<222> LOCATION: (17)..(17)
<223> OTHER INFORMATION: 2'-fluoroadenosine
<220> FEATURE:
<221> NAME/KEY: modified_base
<222> LOCATION: (18)..(18)
<223> OTHER INFORMATION: cm
<220> FEATURE:
<221> NAME/KEY: misc_feature
<222> LOCATION: (19)..(19)
<223> OTHER INFORMATION: 2'-fluorouridine
<220> FEATURE:
<221> NAME/KEY: modified_base
<222> LOCATION: (20)..(20)
<223> OTHER INFORMATION: gm
<220> FEATURE:
<221> NAME/KEY: misc_feature
<222> LOCATION: (21)..(21)
<223> OTHER INFORMATION: 2'-fluoroguanosine
<220> FEATURE:
<221> NAME/KEY: misc_feature
<222> LOCATION: (22)..(22)
<223> OTHER INFORMATION: 2'-O-methyladenosine
<220> FEATURE:
<221> NAME/KEY: misc_feature
<222> LOCATION: (23)..(23)
<223> OTHER INFORMATION: 2'-fluorocytidine
<220> FEATURE:
<221> NAME/KEY: misc_feature
<222> LOCATION: (24)..(24)
<223> OTHER INFORMATION: 2'-O-methylthymidine
<220> FEATURE:
```

<221> NAME/KEY: misc_feature
<222> LOCATION: (25)..(25)
<223> OTHER INFORMATION: 2'-fluorothymidine

<400> SEQUENCE: 10
agggauuccu gggaaaacug gactt    25

<210> SEQ ID NO 11
<211> LENGTH: 25
<212> TYPE: DNA
<213> ORGANISM: Artificial Sequence
<220> FEATURE:
<223> OTHER INFORMATION: Combined DNA/RNA molecule
<220> FEATURE:
<221> NAME/KEY: modified_base
<222> LOCATION: (1)..(1)
<223> OTHER INFORMATION: gm
<220> FEATURE:
<221> NAME/KEY: misc_feature
<222> LOCATION: (2)..(2)
<223> OTHER INFORMATION: 2'-fluorouridine
<220> FEATURE:
<221> NAME/KEY: modified_base
<222> LOCATION: (3)..(3)
<223> OTHER INFORMATION: cm
<220> FEATURE:
<221> NAME/KEY: misc_feature
<222> LOCATION: (4)..(4)
<223> OTHER INFORMATION: 2'-fluorocytidine
<220> FEATURE:
<221> NAME/KEY: misc_feature
<222> LOCATION: (5)..(5)
<223> OTHER INFORMATION: 2'-O-methyladenosine
<220> FEATURE:
<221> NAME/KEY: misc_feature
<222> LOCATION: (6)..(6)
<223> OTHER INFORMATION: 2'-fluoroguanosine
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
<223> OTHER INFORMATION: 2'-fluorouridine
<220> FEATURE:
<221> NAME/KEY: modified_base
<222> LOCATION: (9)..(9)
<223> OTHER INFORMATION: um
<220> FEATURE:
<221> NAME/KEY: misc_feature
<222> LOCATION: (10)..(10)
<223> OTHER INFORMATION: 2'-fluorouridine
<220> FEATURE:
<221> NAME/KEY: modified_base
<222> LOCATION: (11)..(11)
<223> OTHER INFORMATION: cm
<220> FEATURE:
<221> NAME/KEY: misc_feature
<222> LOCATION: (12)..(12)
<223> OTHER INFORMATION: 2'-fluorocytidine
<220> FEATURE:
<221> NAME/KEY: modified_base
<222> LOCATION: (13)..(13)
<223> OTHER INFORMATION: cm
<220> FEATURE:
<221> NAME/KEY: misc_feature
<222> LOCATION: (14)..(14)
<223> OTHER INFORMATION: 2'-fluoroadenosine
<220> FEATURE:
<221> NAME/KEY: modified_base
<222> LOCATION: (15)..(15)
<223> OTHER INFORMATION: gm
<220> FEATURE:
<221> NAME/KEY: misc_feature
<222> LOCATION: (16)..(16)
<223> OTHER INFORMATION: 2'-fluoroguanosine

```
<220> FEATURE:
<221> NAME/KEY: misc_feature
<222> LOCATION: (17)..(17)
<223> OTHER INFORMATION: 2'-O-methyladenosine
<220> FEATURE:
<221> NAME/KEY: misc_feature
<222> LOCATION: (18)..(18)
<223> OTHER INFORMATION: 2'-fluoroadenosine
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: 2'-fluorocytidine
<220> FEATURE:
<221> NAME/KEY: modified_base
<222> LOCATION: (21)..(21)
<223> OTHER INFORMATION: cm
<220> FEATURE:
<221> NAME/KEY: misc_feature
<222> LOCATION: (22)..(22)
<223> OTHER INFORMATION: 2'-fluorocytidine
<220> FEATURE:
<221> NAME/KEY: modified_base
<222> LOCATION: (23)..(23)
<223> OTHER INFORMATION: um
<220> FEATURE:
<221> NAME/KEY: misc_feature
<222> LOCATION: (24)..(24)
<223> OTHER INFORMATION: 2'-fluorothymidine
<220> FEATURE:
<221> NAME/KEY: misc_feature
<222> LOCATION: (25)..(25)
<223> OTHER INFORMATION: 2'-O-methylthymidine

<400> SEQUENCE: 11
guccaguuuu cccaggaauc ccutt                                    25

<210> SEQ ID NO 12
<211> LENGTH: 25
<212> TYPE: DNA
<213> ORGANISM: Artificial Sequence
<220> FEATURE:
<223> OTHER INFORMATION: Combined DNA/RNA molecule
<220> FEATURE:
<221> NAME/KEY: misc_feature
<222> LOCATION: (1)..(1)
<223> OTHER INFORMATION: 2'-O-methyladenosine
<220> FEATURE:
<221> NAME/KEY: misc_feature
<222> LOCATION: (2)..(2)
<223> OTHER INFORMATION: 2'-fluoroguanosine
<220> FEATURE:
<221> NAME/KEY: modified_base
<222> LOCATION: (3)..(3)
<223> OTHER INFORMATION: gm
<220> FEATURE:
<221> NAME/KEY: misc_feature
<222> LOCATION: (4)..(4)
<223> OTHER INFORMATION: 2'-fluoroguanosine
<220> FEATURE:
<221> NAME/KEY: misc_feature
<222> LOCATION: (5)..(5)
<223> OTHER INFORMATION: 2'-O-methyladenosine
<220> FEATURE:
<221> NAME/KEY: misc_feature
<222> LOCATION: (6)..(6)
<223> OTHER INFORMATION: 2'-fluorouridine
<220> FEATURE:
<221> NAME/KEY: modified_base
<222> LOCATION: (7)..(7)
<223> OTHER INFORMATION: um
<220> FEATURE:
<221> NAME/KEY: misc_feature
<222> LOCATION: (8)..(8)
```

```
<223> OTHER INFORMATION: 2'-fluorocytidine
<220> FEATURE:
<221> NAME/KEY: modified_base
<222> LOCATION: (9)..(9)
<223> OTHER INFORMATION: cm
<220> FEATURE:
<221> NAME/KEY: misc_feature
<222> LOCATION: (10)..(10)
<223> OTHER INFORMATION: 2'-fluorouridine
<220> FEATURE:
<221> NAME/KEY: modified_base
<222> LOCATION: (11)..(11)
<223> OTHER INFORMATION: gm
<220> FEATURE:
<221> NAME/KEY: misc_feature
<222> LOCATION: (12)..(12)
<223> OTHER INFORMATION: 2'-fluoroguanosine
<220> FEATURE:
<221> NAME/KEY: modified_base
<222> LOCATION: (13)..(13)
<223> OTHER INFORMATION: gm
<220> FEATURE:
<221> NAME/KEY: misc_feature
<222> LOCATION: (14)..(14)
<223> OTHER INFORMATION: 2'-fluoroadenosine
<220> FEATURE:
<221> NAME/KEY: misc_feature
<222> LOCATION: (15)..(15)
<223> OTHER INFORMATION: 2'-O-methyladenosine
<220> FEATURE:
<221> NAME/KEY: misc_feature
<222> LOCATION: (16)..(16)
<223> OTHER INFORMATION: 2'-fluoroadenosine
<220> FEATURE:
<221> NAME/KEY: misc_feature
<222> LOCATION: (17)..(17)
<223> OTHER INFORMATION: 2'-O-methyladenosine
<220> FEATURE:
<221> NAME/KEY: misc_feature
<222> LOCATION: (18)..(18)
<223> OTHER INFORMATION: 2'-fluorocytidine
<220> FEATURE:
<221> NAME/KEY: modified_base
<222> LOCATION: (19)..(19)
<223> OTHER INFORMATION: um
<220> FEATURE:
<221> NAME/KEY: misc_feature
<222> LOCATION: (20)..(20)
<223> OTHER INFORMATION: 2'-fluoroguanosine
<220> FEATURE:
<221> NAME/KEY: modified_base
<222> LOCATION: (21)..(21)
<223> OTHER INFORMATION: gm
<220> FEATURE:
<221> NAME/KEY: misc_feature
<222> LOCATION: (22)..(22)
<223> OTHER INFORMATION: 2'-fluoroadenosine
<220> FEATURE:
<221> NAME/KEY: modified_base
<222> LOCATION: (23)..(23)
<223> OTHER INFORMATION: cm
<220> FEATURE:
<221> NAME/KEY: misc_feature
<222> LOCATION: (24)..(24)
<223> OTHER INFORMATION: 2'-O-methylthymidine
<220> FEATURE:
<221> NAME/KEY: misc_feature
<222> LOCATION: (25)..(25)
<223> OTHER INFORMATION: 2'-fluorothymidine

<400> SEQUENCE: 12
agggauuccu gggaaaacug gactt                                              25

<210> SEQ ID NO 13
<211> LENGTH: 23
<212> TYPE: RNA
<213> ORGANISM: Artificial Sequence
```

```
<220> FEATURE:
<223> OTHER INFORMATION: Polynucleotide

<400> SEQUENCE: 13
agggauuccu gggaaaacug gac                                              23

<210> SEQ ID NO 14
<211> LENGTH: 23
<212> TYPE: RNA
<213> ORGANISM: Artificial Sequence
<220> FEATURE:
<223> OTHER INFORMATION: Polynucleotide

<400> SEQUENCE: 14
agggauuccu gggaaaacug gac                                              23

<210> SEQ ID NO 15
<211> LENGTH: 23
<212> TYPE: RNA
<213> ORGANISM: Artificial Sequence
<220> FEATURE:
<223> OTHER INFORMATION: Polynucleotide

<400> SEQUENCE: 15
guccaguuuu cccaggaauc ccu                                              23

<210> SEQ ID NO 16
<211> LENGTH: 23
<212> TYPE: RNA
<213> ORGANISM: Artificial Sequence
<220> FEATURE:
<223> OTHER INFORMATION: Polynucleotide
<220> FEATURE:
<221> NAME/KEY: misc_feature
<222> LOCATION: (1)..(1)
<223> OTHER INFORMATION: 2'-fluoroguanosine
<220> FEATURE:
<221> NAME/KEY: modified_base
<222> LOCATION: (2)..(2)
<223> OTHER INFORMATION: gm
<220> FEATURE:
<221> NAME/KEY: misc_feature
<222> LOCATION: (3)..(3)
<223> OTHER INFORMATION: 2'-fluoroadenosine
<220> FEATURE:
<221> NAME/KEY: modified_base
<222> LOCATION: (4)..(4)
<223> OTHER INFORMATION: um
<220> FEATURE:
<221> NAME/KEY: misc_feature
<222> LOCATION: (5)..(5)
<223> OTHER INFORMATION: 2'-fluorouridine
<220> FEATURE:
<221> NAME/KEY: modified_base
<222> LOCATION: (6)..(6)
<223> OTHER INFORMATION: cm
<220> FEATURE:
<221> NAME/KEY: misc_feature
<222> LOCATION: (7)..(7)
<223> OTHER INFORMATION: 2'-fluorocytidine
<220> FEATURE:
<221> NAME/KEY: modified_base
<222> LOCATION: (8)..(8)
<223> OTHER INFORMATION: um
<220> FEATURE:
<221> NAME/KEY: misc_feature
<222> LOCATION: (9)..(9)
<223> OTHER INFORMATION: 2'-fluoroguanosine
<220> FEATURE:
<221> NAME/KEY: modified_base
<222> LOCATION: (10)..(10)
<223> OTHER INFORMATION: gm
<220> FEATURE:
```

```
<221> NAME/KEY: misc_feature
<222> LOCATION: (11)..(11)
<223> OTHER INFORMATION: 2'-fluoroadenosine
<220> FEATURE:
<221> NAME/KEY: misc_feature
<222> LOCATION: (12)..(12)
<223> OTHER INFORMATION: 2'-O-methyladenosine
<220> FEATURE:
<221> NAME/KEY: misc_feature
<222> LOCATION: (13)..(13)
<223> OTHER INFORMATION: 2'-fluoroadenosine
<220> FEATURE:
<221> NAME/KEY: modified_base
<222> LOCATION: (14)..(14)
<223> OTHER INFORMATION: um
<220> FEATURE:
<221> NAME/KEY: misc_feature
<222> LOCATION: (15)..(15)
<223> OTHER INFORMATION: 2'-fluoroadenosine
<220> FEATURE:
<221> NAME/KEY: modified_base
<222> LOCATION: (16)..(16)
<223> OTHER INFORMATION: cm
<220> FEATURE:
<221> NAME/KEY: misc_feature
<222> LOCATION: (17)..(17)
<223> OTHER INFORMATION: 2'-fluorouridine
<220> FEATURE:
<221> NAME/KEY: modified_base
<222> LOCATION: (18)..(18)
<223> OTHER INFORMATION: gm
<220> FEATURE:
<221> NAME/KEY: misc_feature
<222> LOCATION: (19)..(19)
<223> OTHER INFORMATION: 2'-fluorouridine
<220> FEATURE:
<221> NAME/KEY: modified_base
<222> LOCATION: (20)..(20)
<223> OTHER INFORMATION: um
<220> FEATURE:
<221> NAME/KEY: misc_feature
<222> LOCATION: (21)..(21)
<223> OTHER INFORMATION: 2'-fluorocytidine
<220> FEATURE:
<221> NAME/KEY: modified_base
<222> LOCATION: (22)..(22)
<223> OTHER INFORMATION: um
<220> FEATURE:
<221> NAME/KEY: modified_base
<222> LOCATION: (23)..(23)
<223> OTHER INFORMATION: um

<400> SEQUENCE: 16
ggauuccugg aaauacuguu cuu                                            23
```

US 10,874,688 B2

DOUBLE-STRANDED NUCLEIC ACID MOLECULE AND USE THEREOF

CROSS REFERENCE TO RELATED APPLICATION

This Application is a 371 of PCT/JP2017/039364 filed on Oct. 31, 2017, which, in turn, claimed the priority of Japanese Patent Application No. 2016-213131 filed on Oct. 31, 2016, both applications are incorporated herein by reference.

TECHNICAL FIELD

The present invention relates to a novel double-stranded nucleic acid molecule and use thereof. More particularly, the invention relates to an miR-145-like double-stranded nucleic acid molecule, an expression vector of the nucleic acid molecule, an antitumor agent including these, and a method for preventing and/or treating a tumor by utilizing these.

BACKGROUND ART miRNA is a cellular endogenous non-coding RNA about 20 to 25 bases long. miRNA is first transcribed as a primary transcript (pri-miRNA) having a length of about several hundred to several thousand bases, from miRNA gene on the genomic DNA. Next, the primary transcript is processed to become pre-miRNA having a hairpin structure having a length of about several dozen bases. Subsequently, the pre-miRNA moves from the nucleus into the cytoplasm and is further processed to become mature miRNA comprising a dimer (a guide strand and a passenger strand) each about 20 to 25 bases long. It is known that mature miRNA functions to inhibit translation of a target gene as the guide strand (antisense strand) in the mature miRNA forms a complex with a protein called RISC (RNA-Induced Silencing Complex) and acts on the mRNA of the target gene.

miRNA is known to have various functions in the cell; however, it is known that the amount of certain kinds of miRNA are decreased in a lesioned tissue of a cancer patient, and antitumor activity is shown by increasing the amount thereof.

miR-145 is one kind of miRNA exhibiting such antitumor activity, is targeted at a plurality of genes related to the cell cycle, cell proliferation, invasion of cancer cells, cell death, or the like, and is considered as one of tumor suppressors. Regarding miR-145, it is also known that the amount of expression is decreased in various tumors such as urinary bladder cancer, colon cancer, breast cancer, leukemia, ovarian cancer, prostate cancer, liver cancer (for example, Hepatocarcinoma), lung cancer (for example, non-small cell lung cancer), stomach cancer, esophageal cancer, pancreatic cancer, neuroglioma, pharyngeal cancer, nasopharyngeal cancer, oral cancer, and pituitary tumor (Non-Patent Literature 1). For example, it has been reported that by inducing the expression of miR-145, the cell survival rates of urinary bladder cells, prostate cancer cells, and pancreatic cancer cells are decreased (Non-Patent Literatures 2, 5, and 8), proliferation of colon cancer cells and breast cancer cells is suppressed (Non-Patent Literatures 3 and 6), or invasion of stomach cancer cells (Non-Patent Literature 7) is suppressed. Furthermore, an example in which leukemia developed by suppressing the expression of miR-145 has also been reported (Non-Patent Literature 4).

CITATION LIST

Non-Patent Literatures

Non-Patent Literature 1: Shi-Yun Cui et al., Journal of Cellular and Molecular Medicine (2014) 18, 1913-1926
Non-Patent Literature 2: M S Ostenfeld et al., Oncogene (2010) 29, 1073-1084
Non-Patent Literature 3: Lea H. Gregersen et al., Plos ONE (2010) 5, e8836
Non-Patent Literature 4: Daniel T. Starczynowski et al., Blood (2011) 117, 595-607
Non-Patent Literature 5: M S Zaman et al., British Journal of Cancer (2010) 103, 256-264
Non-Patent Literature 6: Shihua Wang et al., International Journal of Oncology (2009) 34, 1461-1466.
Non-Patent Literature 7: Shi-Bin Jiang et al., OncoTargets and Therapy (2016) 2016, 2305-2315
Non-Patent Literature 8: Sheema Khan et al., Oncotarget (2016) 5, 7599-7609

SUMMARY OF INVENTION

As described above, miR-145 is expected as an active ingredient for antitumor agents. While the present inventor conducted a study on miR-145, the inventor artificially modified the nucleotide sequence of the passenger strand of miR-145 and thereby found surprisingly that a double-stranded nucleic acid molecule produced into a polynucleotide chain including a nucleotide sequence that is perfectly complementary to the guide strand exhibits excellent antitumor activity. Thus, the inventor completed the present invention.

DESCRIPTION OF EMBODIMENTS

Figure 1:
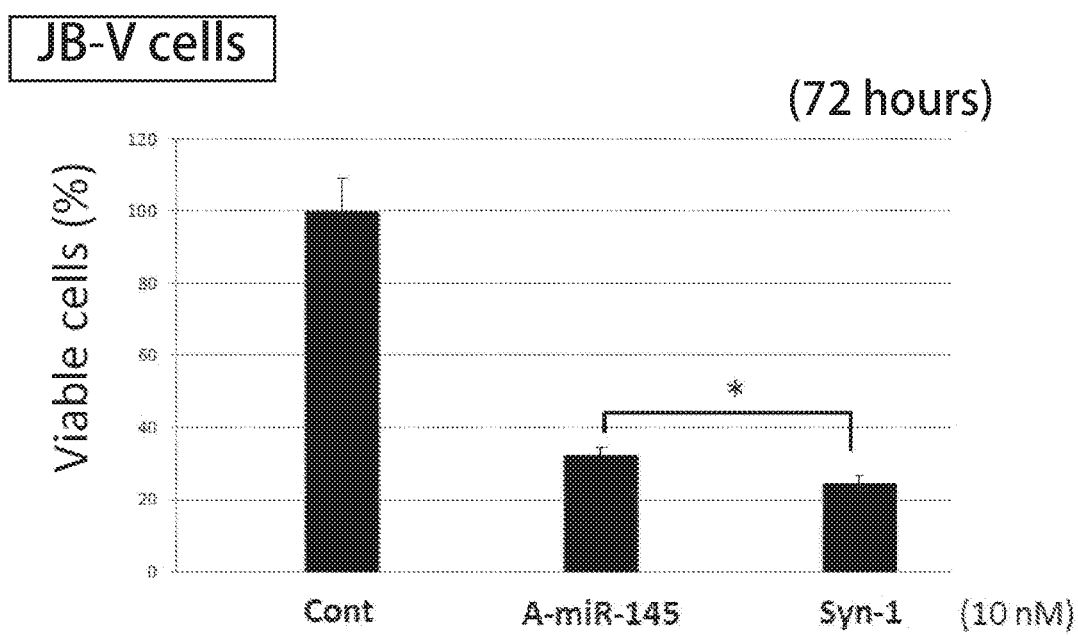
FIG. 1 shows the results of an evaluation of the viable cell count in Test Example 1.

Embodiments of the present invention will be described below. Meanwhile, the present invention is not intended to be limited to the following embodiments.
In the present specification, the expression "X to Y" representing a range means "more than or equal to X and less than or equal to Y". Furthermore, unless particularly stated otherwise, operations, the measurement of physical properties, or the like are carried out under the conditions of room temperature (20 to 25° C.)/a relative humidity of 40 to 50% RH.

<<Double-Stranded Nucleic Acid Molecule>>

An aspect of the present invention relates to a double-stranded nucleic acid molecule including a first polynucleotide chain including a predetermined base sequence and a second polynucleotide chain including a base sequence that is complementary to the first polynucleotide chain (hereinafter, also referred to as "nucleic acid molecule according to the present invention").

<First Polynucleotide Chain>

According to the present invention, a first polynucleotide chain includes a base sequence represented by the following Chemical Formula (1) (SEQ ID NO:1):

```
Chemical Formula (1):
                                    SEQ ID NO: 1
5'-AGGGA(T/U)(T/U)CC(T/U)GGGAAAAC(T/U)GGACNN-
(L-M)_k-3'
``` provided that in the Chemical Formula (1), (T/U) represents T or U; and Ns each independently represent A, C, G, T, U, or a deletion.

The nucleic acid molecule according to the present invention may be a product that has been subjected to chemical modification by means that are known to those ordinarily skill in the art, for the purpose of incorporation into cells, enhancement of the resistance to RNase, and the like. Examples of such chemical modification include: (a) addition of a chemically modifying group to the 3'-terminal of the first polynucleotide chain or the second polynucleotide chain, (b) substitution of a constituent base with a base containing a modified sugar moiety, (c) substitution of a phosphodiester bond with a phosphorus atom-modified bond, and the like.

(a) Addition of Chemically Modifying Group to 3'-Terminal

Among these, subjecting the first polynucleotide chain to the chemical modification of (a) (addition of chemically modifying group to the 3'-terminal) corresponds to the case where in the Chemical Formula (1), k is 1. In this case, specifically, a group having a structure represented by "-L-M" is bonded to an oxygen atom of a phosphodiester bond on the 3'-terminal side, which is bonded to the base of a nucleotide at the 3'-terminal of the first polynucleotide chain. When k in the Chemical Formula (1) is 1, L represents a substituted or unsubstituted cyclic compound-containing group represented by any one of the following Chemical Formulas (2a) to (2g):

(2a)
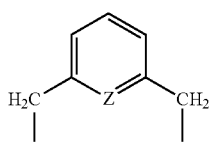

(2b)
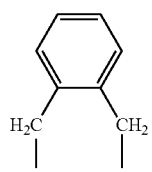

-continued (2c)

(2d)
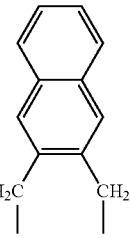

(2e)
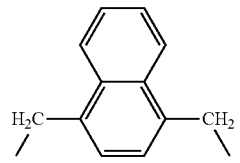

(2f)
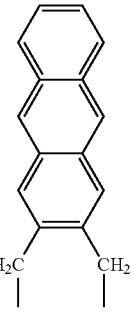

(2g)
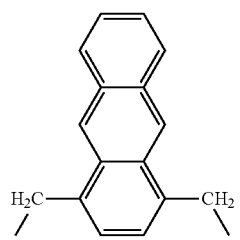

or represents a divalent group formed by two or more of the above-mentioned cyclic compound-containing groups are respectively linked through a phosphodiester bond; and M represents a hydroxyl group or a —O-hydroxyl protective group.

According to a preferred embodiment, the L represents a divalent group formed by two or more of the above-mentioned cyclic compound-containing groups (for example, 2 to 10 groups, preferably 2 to 6 groups, more preferably 2 to 4 groups, even more preferably 2 to 3 groups, and particularly preferably 2 groups) respectively linked through a phosphodiester bond.

Here, in a case where the cyclic compound-containing group is substituted, examples of the substituent that substitutes the cyclic compound-containing group include a halogen such as fluorine, chlorine, bromine, and iodine; an alkyl group such as a methyl group, an ethyl group, a tert-butyl group, and a dodecyl group; an aryl group such as a phenyl group, a p-tolyl group, a xylyl group, a cumenyl group, a naphthyl group, an anthryl group, and a phenanthryl group; an alkoxy group such as a methoxy group, an ethoxy group, and a tert-butoxy group; an aryloxy group such as a phenoxy group and a p-tolyloxy group; an alkoxycarbonyl group such as a methoxycarbonyl group, a butoxycarbonyl group, a 2-ethylhexyloxycarbonyl group, and a phenoxycarbonyl group; an acyloxy group such as an acetoxy group, a propionyloxy group, and a benzoyloxy group; an acyl group such as an acetyl group, a benzoyl group, an isobutyryl group, an acryloyl group, a methacryloyl group, and a methoxalyl group; an alkylsulfanyl group such as a methylsulfanyl group, and a tert-butylsulfanyl group; an arylsulfanyl group such as a phenylsulfanyl group, and a p-tolylsulfanyl group; an alkylamino group such as a methylamino group and a cyclohexylamino group; a dialkylamino group such as a dimethylamino group, a diethylamino group, a morpholino group, and a piperidino group; an arylamino group such as a phenylamino group and a p-tolylamino group; as well as a hydroxy group, a carboxy group, a formyl group, a mercapto group, a sulfo group, a mesyl group, a p-toluenesulfonyl group, an amino group, a nitro group, a cyano group, a trifluoromethyl group, a trichloromethyl group, a trimethylsilyl group, a phosphinico group, a phosphono group, and the like.

Furthermore, in the Chemical Formula (2a), Z represents CH or N. According to a preferred embodiment, the L includes one or two or more cyclic compound-containing groups represented by the Chemical Formula (2a), which may be substituted. Furthermore, according to another preferred embodiment, the L represents a divalent group in which two or more cyclic compound-containing groups (for example, 2 to 10 groups, preferably 2 to 6 groups, more preferably 2 to 4 groups, even more preferably 2 to 3 groups, and particularly preferably 2 groups) represented by the Chemical Formula (2a) are respectively linked through a phosphodiester bond. At this time, L is preferably a divalent group that includes, among the cyclic compound-containing groups represented by the Chemical Formula (2a), both a group in which Z is CH (that is, a group containing a benzene ring) and a group in which Z is N (that is, a group containing a pyridine ring); and more preferably a divalent group formed from one each of these groups. Furthermore, according to a more preferred embodiment, the L has a structure represented by the following Chemical Formula (3):

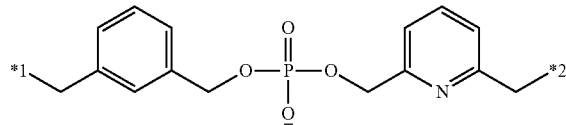

(3)

Here, in the Chemical Formula (3), *1 represents a bonding site to an oxygen atom of a phosphodiester bond on the 3'-terminal side bonded to the base of a nucleotide of the 3'-terminal of the polynucleotide chain; and *2 represents a bonding site to M.

In the Chemical Formula (1), M represents a hydroxyl group or a —O-hydroxyl protective group, and preferably represents a hydroxyl group. Therefore, according to the most preferred embodiment, the structure represented by "-L-M" is a group in which a hydroxyl group is bonded to *2 of the above-described Chemical Formula (3) (see the Examples that will be described below). Meanwhile, the hydroxyl protective group may be a group that protects oxygen in a hydroxyl group that is substituted by the relevant protective group from an unintended reaction, and conventionally known findings can be referred to as appropriate. Preferably, a hydroxyl protective group is a group that maintains the activity of an oligonucleotide derivative and is removed. Such a hydroxyl protective group is not particularly limited; however, examples include a fluorenylmethoxycarbonyl (FMOC) group, a dimethoxytrityl (DMT) group, a monomethoxytrityl group, a trifluoroacetyl group, a levulinyl group, or a silyl group.

(b) Substitution of Constituent Base with Base Containing Modified Sugar Moiety

In a case where the first polynucleotide chain is subjected to the chemical modification of (b) (substitution of a constituent base with a base containing a modified sugar moiety), the various nucleotides that constitute the first polynucleotide strand can be each independently substituted with a base containing a modified sugar moiety selected from the group consisting of 2'-O-methyl, 2-methoxyethoxy, 2'-fluoro, 2'-allyl, 2'-O-[2 (methylamino)-2-oxoethyl], 4'-thio, 4'-(CH$_2$)$_2$—O-2'-crosslinking, 2'-locked nucleic acid, or 2'-O—(N-methylcarbamate). Among them, it is preferable that the modifying sugar moiety includes 2'-O-methyl or 2'-fluoro modification.

(c) Substitution of Phosphodiester Bond with Phosphorus Atom-Modified Bond

In a case where the first polynucleotide chain is subjected to the chemical modification of (c) (substitution of a phosphodiester bond with a phosphorus atom-modified bond), the phosphodiester bonds that constitute the first polynucleotide chain can be each independently substituted by a phosphorus atom-modified bond represented by the following Chemical Formula (4):

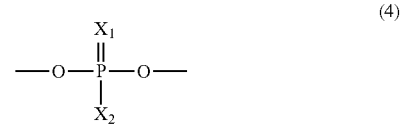

(4)

In the Chemical Formula (4), $X^1$ independently represents O, S, or Se; and $X^2$ independently represents OH or O$^-$, SH or S$^-$, SeH or Se$^-$, an alkyl group having 1 to 4 carbon atoms, or a morpholino group. However, in a case where $X^1$ represents O and $X^2$ represents O$^-$, the Chemical Formula (4) represents a conventional phosphodiester bond. Therefore, such a case is not to be included in the scope of the present invention. According to a preferred embodiment, $X^1$ represents O, and $X^2$ represents SH or S$^-$, SeH or Se$^-$, an alkyl group having 1 to 4 carbon atoms, or a morpholino group. Furthermore, according to a more preferred embodiment, $X^1$ represents O, and $X^2$ represents SH or S$^-$. Furthermore, according to a particularly preferred embodiment, $X^1$ represents O, and $X^2$ represents SH or S$^-$ (in this case, the phosphorus atom-modified bond is a phosphorothioate bond).

Endogenous mature miR-145 is known to have a base sequence that is common in the human being and many non-human animals, and the guide strand (antisense strand, miR-145-5p) and the passenger strand (sense strand, miR-145-3p) lack complementarity in some portion of the respective base sequences (see the following Table 1). Meanwhile, the first polynucleotide strand of the nucleic acid molecule according to the present invention includes a nucleotide sequence which is perfectly complementary to the guide strand of the endogenous mature miR-145 (having a polynucleotide sequence set forth in SEQ ID NO:8), and the nucleotide sequence corresponds to the portion of "AGGGA(T/U)(T/U)CC(T/U)GGGAAAAC(T/U) GGAC" in SEQ ID NO:1. Hereinafter, a region of the first polynucleotide chain that is perfectly complementary to the polynucleotide sequence set forth in SEQ ID NO:8 may be referred to as "complementarity region". The detailed mechanism by which such a nucleic acid molecule exhibits excellent antitumor activity is not clearly understood; however, it is speculated that the three-dimensional structure of the nucleic acid molecule could be related to the induction of apoptosis of cancer cells.

The "double-stranded nucleic acid molecule" according to the present specification is a nucleic acid molecule containing a hybrid structure of a first polynucleotide chain and a second polynucleotide chain (perfectly matching base sequences) in the molecular structure. The double-stranded nucleic acid molecule may be one having a structure in which a first polynucleotide chain that is a single strand, and a second polynucleotide chain that is likewise a single strand, are hybridized. Alternatively, as is the case of pri-miRNA or pre-miRNA, which is precursors of endogenous miRNA, a hairpin structure in which a first polynucleotide chain and a second polynucleotide chain are linked through a loop region is also acceptable. The length of such a loop region is not particularly limited as long as the purpose and effect of the present invention are not impaired; however, for example, the length is about 3 to 100 bases, and preferably about 3 to 10 bases. The loop region of a nucleic acid molecule having such a hairpin structure can be removed by a processing mechanism related to the maturation of miRNA such as Dicer in the living body.

The "antitumor" in the present specification is interpreted as a term including both the prophylactic action of preventing the development, invasion, metastasis, and/or implantation of a tumor in vitro and/or in vivo, and the therapeutic action that brings suppression of proliferation of tumor cells, annihilation of tumor cells, and/or reduction of tumor. The antitumor activity can be evaluated by, for example, as is described in the Examples, culturing for a desired time period cells that have been transfected with the nucleic acid molecule, and counting the number of cells after culturing.

The numbers of bases of the first polynucleotide chain and the second polynucleotide chain of the nucleic acid molecule according to the present invention may be identical or different. The numbers of bases of the first polynucleotide chain and the second polynucleotide chain of the nucleic acid molecule according to the present invention are, for example, each independently 23 to 30 bases. The numbers of bases of the first polynucleotide chain and the second polynucleotide chain of the nucleic acid molecule according to the present invention are each independently preferably 23 to 27 bases, more preferably 23 to 25 bases, and even more preferably 25 bases.

The first polynucleotide chain of the nucleic acid molecule according to the present invention may be any one of a DNA strand, an RNA strand, or a DNA/RNA chimeric strand; however, from the viewpoint of the antitumor activity, it is preferable that the complementarity region is an RNA strand. That is, according to a preferred embodiment of the present invention, (T/U) in the base sequence set forth in SEQ ID NO:1 is U.

In SEQ ID NO:1, "NN" positioned at the 3'-terminal is a deletion or any arbitrary residue (3'-terminal addition sequence) selected from A, C, G, T, and U, and the respective "N"s may be identical or different. Furthermore, in SEQ ID NO:1, the 3'-terminal addition sequence may be one residue or two residues; however, from the viewpoint of the antitumor activity, the 3'-terminal addition sequence is preferably two residues, and more preferably two residues selected from G and T. Particularly, in a case where NN in the base sequence set forth in SEQ ID NO:1 is GG or TT, it is preferable because high antitumor activity can be exhibited.

<Second Polynucleotide Chain>

The second polynucleotide chain of the nucleic acid molecule according to the present invention is a DNA strand, an RNA strand, or a DNA/RNA chimeric strand, each of which includes a nucleotide sequence that is perfectly complementary to SEQ ID NO:1. From the viewpoint of the antitumor activity, in the second polynucleotide chain, the region that is hybridized with the complementarity region of the first polynucleotide chain (hereinafter, also simply referred to as "hybridization region") is preferably an RNA strand. That is, according to a preferred embodiment, the second polynucleotide chain includes a base sequence represented by the following Chemical Formula (5) (SEQ ID NO:2).

Chemical Formula (5):
SEQ ID NO: 2
5'-GUCCAGUUUUCCCAGGAAUCCCUN'N'-(L-M)$_k$-3'

In the Chemical Formula (5) (SEQ ID NO:2), N's each independently represent A, C, G, T, U, or a deletion.

As described above with regard to the first polynucleotide chain, the second polynucleotide chain may also be a product that has been subjected to chemical modification such as (a) to (c) described above, by means that are known to those ordinarily skill in the art. That is, in the Chemical Formula (5) (SEQ ID NO:2), k, L, and M have the same definitions as the above description (modification of the above-described (a)). Furthermore, the nucleotides that constitute the second polynucleotide chain may be each independently substituted with a base containing a modified sugar moiety selected from the group consisting of 2'-O-methyl, 2'-methoxyethoxy, 2'-fluoro, 2'-allyl, 2'-O-[2(methylamino)-2-oxoethyl], 4'-thio, 4'-(CH$_2$)$_2$—O-2'-crosslinking, 2'-locked nucleic acid, or 2'-O—(N-methylcarbamate) (modification of the above-described (b)), and the phosphodiester bonds that constitute the second polynucleotide chain may be each independently substituted with the phosphorus atom-modified bond represented by the Chemical Formula (3) (modification of the above-described (c)).

In a case where "N'N'" positioned at the 3'-terminal in the SEQ ID NO:2 is a deletion, the base sequence coincides with the guide strand of mature miR-145. In SEQ ID NO:2, from the viewpoint of the antitumor activity, it is preferable that N's are each independently selected from the group consisting of A, C, G, T, and U, and two residues selected from G and T are more preferable. In a case where "N'N'" on the 3'-terminal side in the SEQ ID NO:2 is GG, particularly highly antitumor activity can be exhibited. That is, according to a preferred embodiment of the present invention, N'N' in the base sequence set forth in SEQ ID NO:2 is GG.

In particular, in a case where NN in a base sequence set forth in SEQ ID NO: 1 is GG (that is, the first polynucleotide chain is represented by SEQ ID NO:3 described below), and N'N' in a base sequence set forth in SEQ ID NO:2 is GG (that is, the second polynucleotide chain is represented by SEQ ID NO:4 described below), remarkable antitumor activity can be exhibited.

(Production Method)

The nucleic acid molecule according to the present invention can be chemically synthesized by a conventionally known technique (synthesis according to a phosphoroamidite method of using an automatic nucleic acid synthesizer), based on the base sequence thereof. Furthermore, in regard to the technique of introducing a modified structure represented by "-L-M" described above at the 3'-terminal of one or both of the first polynucleotide chain and the second polynucleotide chain produced as such, conventionally known findings (for example, WO 2007/094135, JP 2011-251912 A, and the like) can be referred to as appropriate. Furthermore, also in regard to a technique of converting a phosphodiester bond at a particular site to the phosphorus atom-modified structure represented by Chemical Formula (3) described above, conventionally known findings can be referred to as appropriate. For example, it is possible to incorporate a phosphorothioate bond instead of the phosphorodiester bond, by performing oxidation of trivalent phosphorus into pentavalence in the final stage of nucleic acid synthesis according to a phosphoroamidite method, using a sulfurizing agent solution instead of an oxidizing agent solution.

An aspect of the present invention relates to a vector including a base sequence that encodes the nucleic acid molecule according to the present invention. Such a vector is not particularly limited as long as it can express the nucleic acid molecule according to the present invention in vivo. For example, it is desirable to use a vector that has been properly selected from a plasmid vector, a viral vector, or the like, which has an appropriate promoter, in accordance with the host into which the vector is to be introduced, and has a DNA encoding the nucleic acid molecule according to the present invention incorporated in the downstream of the promoter by a conventionally known technique. The promoter is not particularly limited; however, for example, examples include U6 promoter, H1 RNA polymerase III promoter, SV40 promoter, LTR promoter, CMV promoter, HSV-TK promoter, and the like.

Examples of the plasmid vector include pSINsi series, pBAsi series, pSIREN series (all manufactured by Takara Bio, Inc.), and the like. A plasmid usually includes a gene resistant to antibiotic substances such as ampicillin and kanamycin.

Regarding the viral vector, for example, for example, examples include a retroviral vector, a lentiviral vector, an adenoviral vector, an adeno-associated viral vector, a vaccinia virus vector, and the like.

The DNA encoding the nucleic acid molecule according to the present invention may be a product in which a DNA encoding the first polynucleotide chain and a DNA encoding the second polynucleotide chain are separately incorporated downstream of respective promoters (tandem type), or may be a product having the above-described hairpin structure in which a DNA encoding a first polynucleotide chain-corresponding region and a DNA encoding a second polynucleotide chain-corresponding region are linked through a DNA encoding a loop region and are incorporated downstream of a single promoter (short hairpin type). It is preferable that a terminator is included downstream of the DNA encoding the nucleic acid molecule according to the present invention.

A method for recombining a DNA encoding the nucleic acid molecule according to the present invention into a vector can be carried out by means that are known to those ordinarily skill in the art, and for example, reference may be made to Sambrook, J et al., Molecular Cloning $2^{nd}$ ed., 9.47-9.58, Cold Spring Harbor Lab. press (1989), and the like.

According to an aspect of the present invention, an antitumor agent including, as an active ingredient, the nucleic acid molecule according to the present invention or the above-described vector that includes a base sequence encoding the nucleic acid molecule according to the present invention, is provided. The antitumor agent can be used for a prophylactic purpose of preventing the development, invasion, metastasis, and/or implantation of a tumor in vitro and/or in vivo, or for a therapeutic purpose of bringing the suppression of proliferation of tumor cells, death of tumor cells, and/or reduction of a tumor. According to an aspect of the present invention, a method for preventing and/or treating a tumor, which includes administering the nucleic acid molecule according to the present invention or the above-described vector including a base sequence encoding the nucleic acid molecule according to the present invention, to a test subject, is provided.

The phrase "including as an active ingredient" according to the present specification means that it is included in an amount sufficient (that is, an effective amount) for exhibiting desired activity (antitumor activity).

The tumors to which the antitumor agent according to the present invention is applied include both benign tumors and malignant tumors, and there are no particular limitations as long as the desired purpose is achieved. However, examples include urinary bladder cancer, colon cancer, breast cancer, leukemia, ovarian cancer, prostate cancer, liver cancer, lung cancer, stomach cancer, esophageal cancer, pancreatic cancer, neuroglioma, pharyngeal cancer, nasopharyngeal cancer, oral cancer, pituitary tumor, bile duct cancer, spleen cancer, renal cancer, uterine cancer, testis cancer, thyroid cancer, brain tumor, hematopoietic tumor, malignant melanoma, and the like. Among these, the antitumor agent according to the present invention can be used particularly effectively for the treatment and/or prevention of urinary bladder cancer, colon cancer, breast cancer, leukemia, ovarian cancer, prostate cancer, liver cancer, lung cancer, stomach cancer, esophageal cancer, pancreatic cancer, neuroglioma, pharyngeal cancer, nasopharyngeal cancer, oral cancer, and pituitary tumor. That is, according to an embodiment of the present invention, an antitumor agent for the prevention and/or treatment of a tumor selected from the group consisting of urinary bladder cancer, colon cancer, breast cancer, leukemia, ovarian cancer, prostate cancer, hepatoma, lung cancer, stomach cancer, esophageal cancer, pancreatic cancer, neuroglioma, pharyngeal cancer, nasopharyngeal cancer, oral cancer, and pituitary tumor is provided. According to another aspect of the present invention, there is provided a method for preventing and/or treating a tumor selected from the group consisting of urinary bladder cancer, colon cancer, breast cancer, leukemia, ovarian cancer, prostate cancer, hepatoma, lung cancer, stomach cancer, esophageal cancer, pancreatic cancer, neuroglioma, pharyngeal cancer, nasopharyngeal cancer, oral cancer, and pituitary tumor, the method including administering the nucleic acid molecule according to the present invention or the above-described vector including a base sequence encoding the nucleic acid molecule according to the present invention to a test subject. The cancer may be primary cancer or metastatic cancer. Furthermore, the "test subject" includes, for example, a human being, and non-human animals such as mouse, rat, hamster, dog, and cat; however, the test subject is preferably a human being.

The antitumor agent according to the present invention can be formulated according to the dosage form as a solid or a liquid. Regarding oral administration, for example, examples include a liquid preparation (an aqueous solution, a non-aqueous solution, or a suspension), a tablet, a bolus, a capsule, a powder, a granular preparation, a paste, and the like. Regarding parenteral administration, for example, the antitumor agent can be formulated into a preparation for subcutaneous, intraperitoneal, or intravenous injection, or a formulation for intravaginal or intrarectal administration. In a case where the active ingredient of the antitumor agent according to the present invention is a nucleic acid molecule, it is preferable that the antitumor agent is formulated in the form of an injectable preparation, and above all, it is more preferable that the antitumor agent is formulated in the form in which a liposome and the nucleic acid molecule form a complex.

By using liposomes, incorporation of the nucleic acid molecule into cells is promoted, and the half-life in blood of the nucleic acid molecule may be prolonged. Regarding the method of producing liposomes, a known method can be employed, and for example, reference may be made to F. Szoka, Annual Review of Biophysics and Bioengineering (1980) 9:467-508, and the like.

Furthermore, for the purpose of further enhancing the bioavailability (and eventually, antitumor activity) than in the case of using liposomes, it is preferable to formulate the nucleic acid molecule according to the present invention into an antitumor agent in the form of a unit structure type pharmaceutical composition (hereinafter, also referred to as "unit structure"). Here, the antitumor agent in the form of a unit structure includes a block copolymer having a cationic polyamino acid segment and a hydrophilic polymer chain segment; and the nucleic acid molecule according to the present invention described above, and the antitumor agent has a structure in which the positive charge of the cationic polyamino acid segment and the negative charge of the double-stranded nucleic acid molecule cancel each other so that the antitumor agent is electrically neutral, and the double-stranded nucleic acid molecule is covered by the hydrophilic polymer chain segment (see WO 2013/162041). As such, by adjusting the relationship between the electric charge amount of the cationic polyamino acid segment and the electric charge amount of the nucleic acid, and covering the nucleic acid with the hydrophilic polymer chain segment, the metabolism or decomposition of the nucleic acid attributed to the electric charge induction or physical (non-charge-dependent) approach to proteins and enzymes in the blood can be prevented. Therefore, the blood retention performance of the nucleic acid on the cationic polymer type carrier is enhanced to a large extent. The details of the unit structure type pharmaceutical composition having such a structure are described in WO 2013/162041; however, a simple explanation will be given below.

According to the present invention, the state in which "the unit structure is electrically neutral" does not exclude a state in which the difference between the sum of charges originating from the cationic groups of the cationic polyamino acid segment in the unit structure and the sum of charges originating from the nucleic acid is in the range of about ±10%, and more strictly in the range of about ±5%. For example, in a case where the sum of charges of the nucleic acid is 40, a state in which the sum of charges originating from the cationic groups in the unit structure is 36 to 44, strictly in the range of 38 to 42, and more strictly in the range of 39 to 41, is not excluded. Meanwhile, in regard to the block copolymer used for the present invention, the hydrophilic polymer chain segment and the cationic polyamino acid segment can respectively exhibit a certain degree of polydispersity. Therefore, in the present specification, when the characteristics (for example, molecular weight, degree of polymerization, and radius of gyration) of the block copolymer are to be mentioned, unless particularly stated otherwise, the mention is made on the average of the polymer as a whole that exhibits polydispersity. Therefore, the electric charge amount will be calculated based on the degree of polymerization, by regarding the degree of polymerization obtainable by making actual measurement as the average degree of polymerization. For example, the degree of polymerization of the cationic polyamino acid segment can be determined by measuring a nuclear magnetic resonance spectrum ($^1$H-NMR spectrum) using a nuclear magnetic resonance apparatus (manufactured by JEOL, Ltd., product name "JNM-ECS400") with solvent: $D_2O$ and temperature: 25° C., and calculating the number of methylene groups of polylysine side chains from the $^1$H-NMR spectrum thus obtained.

In the present specification, the state in which "the nucleic acid is covered by the hydrophilic polymer chain segment" means a state in which the entirety of the nucleic acid is covered by the hydrophilic polymer chain segment. More specifically, a state in which the entirety of the nucleic acid is surrounded in the spatial expanse (radius of gyration) of the hydrophilic polymer chain segments, is meant. In a case where the unit structure is formed by a plurality of pieces of block copolymers, it is not necessary that the hydrophilic polymer chain segment of one piece of the block copolymer covers the entirety of the nucleic acid, and it is desirable that the entirety of the nucleic acid is surrounded in a comprehensive spatial expanse originating from the hydrophilic polymer chain segments of the respective block copolymers.

In regard to the unit structure, the cationic polyamino acid segment may be in the form of being disposed in a linear configuration along the direction of growth of the nucleic acid; however, the state of disposition of the cationic polyamino acid segment is not restricted with regard to the limitation by which the negative charge of the nucleic acid can be canceled, and for example, a form in which the cationic polyamino acid segment is disposed so as to be wound along the helical structure of the nucleic acid is also possible.

The unit structure has one feature that many and unspecified block copolymers and one or a plurality of nucleic acids are included, and unlike conventional complexes for which it is difficult to specify the composition (for example, conventional nucleic acid-enclosed core-shell type polymer micelles), the block copolymers and the nucleic acids are respectively included in predetermined content numbers that are determined based on the respective electric charge amounts. According to a certain embodiment, the unit structure can include m×N pieces of nucleic acids and n×N pieces of block copolymers (here, N is an integer of 1 or greater, and m and n are each independently, for example, an integer from 1 to 9). Meanwhile, the number of nucleic acids included in the unit structure can be determined by measuring the number of fluorescent molecules originating from Cy5-siRNA at room temperature in a 10 mM HEPES buffer solution including 150 mM NaCl, by fluorescence correlation spectroscopy using a confocal laser scanning microscope (manufactured by Carl Zeiss AG, product name "LSM510") equipped with a 40× object lens (C-Apochromat, manufactured by Carl Zeiss AG) and a ConfoCor3 module, and calculating the number based on the number of fluorescent molecules at the time of nucleic acids only. On the other hand, the number of the block copolymers included in the unit structure can be calculated by further using the value of the molecular weight of the unit structure measured at 20° C. in a 10 mM HEPES buffer solution including 150 mMNaCl using an analytical ultracentrifuge (manufactured by Beckman Coulter, Inc., product name "Optima XL-A", in addition to the degree of polymerization of the cationic polyamino acid segment and the number of nucleic acids in the unit structure described above.

The number of the block copolymers included in the unit structure is not limited as long as the block copolymers can constitute an electrically neutral unit structure with nucleic acids and are capable of covering the nucleic acids by means of spatial expanse of the hydrophilic polymer chain segments, and for example, the number may be an integer from 1 to 8. Meanwhile, the unit structure can be constructed using two or more block copolymers; however, the unit structure may also be constructed using one block copolymer.

A block copolymer that can form a unit structure has a cationic polyamino acid segment and a hydrophilic polymer chain segment. According to a certain embodiment, the cationic polyamino acid segment has a positive charge that cancels the negative charge of the nucleic acid to be included in the unit structure and electrically neutralizes the unit structure, and the hydrophilic polymer chain segment has a chain length that covers the nucleic acid. The hydrophilic polymer chain segment can be disposed, for example, at the end (one end or both ends) of the cationic polyamino acid segment. Furthermore, instead of the end or in addition to this, the hydrophilic polymer chain segment may be grafted to a side chain of a middle portion (preferably, approximately central portion) of the cationic polyamino acid segment, or may be disposed between two adjacent cationic polyamino acid segments. In a case where the hydrophilic polymer chain segment is disposed between two adjacent cationic polyamino acid segments, it is preferable that the hydrophilic polymer chain segment is disposed so as to grow in a direction that intersects the direction of arrangement of these cationic polyamino acid segments.

The block copolymer preferably has a plurality of hydrophilic polymer chain segments (for example, having two or more hydrophilic polymer chain segments per one block copolymer). When a block copolymer having a plurality of hydrophilic polymer chain segments is used, since the nucleic acid can be covered more strictly, metabolism or decomposition by enzymes and the like can be suitably avoided. As a result, a unit structure having superior blood retentivity can be obtained. The number of hydrophilic polymer chain segments to be disposed at each site may be, for example, 1 to 4. The hydrophilic polymer chain segment may be in a state in which a plurality is disposed by a polybranched hydrophilic polymer structure. The number of hydrophilic polymer chain segments that are disposed in the block copolymer may be 4 or more. More specifically, in a case where the unit structure is formed by one block copolymer, this one block copolymer may have four or more hydrophilic polymer chain segments (for example, one block copolymer can have two hydrophilic polymer chain segments at each of the two ends of the cationic polyamino acid segment). Furthermore, the block copolymer may further have, if necessary, a target binding site bonded to the hydrophilic polymer chain-side terminal. By having a target binding site, reachability of the nucleic acid to a desired site that becomes a target by having a target binding site can be enhanced. Meanwhile, in the present specification, the block copolymer is to include also a pharmaceutically acceptable salt of the block copolymer.

As the amino acid that constitutes the cationic polyamino acid segment, any arbitrary appropriate cationic amino acid having a cationic group (representatively, an amino group, and preferably, a primary amino group) in a side chain can be used. Examples include basic amino acids such as lysine, arginine, histidine, and ornithine; and amino acid derivatives having a cationic group introduced into acidic amino acids such as aspartic acid and glutamic acid. Since the negative charge of a nucleic acid originates from a phosphoric acid group (or phosphorus atom-modified group), a nucleic acid has one negative charge (electric charge amount=−1) at an approximately equal interval. Therefore, from the viewpoint of suitably forming an electrostatic bond with each phosphoric acid group in the nucleic acid, an amino acid having one cationic group in the side chain, and more specifically, an amino acid having one positive electric charge in the side chain at the blood pH, can be preferably used.

In regard to the cationic polyamino acid segment, it is preferable that the distance from the main chain to the cationic group on the side chain is short. Specifically, it is preferable that the cationic group is bonded to the main chain preferably through 1 to 6, and more preferably 2 to 4, atoms. It is because the blood retentivity of the unit structure (consequently, blood retentivity of the nucleic acid) can be enhanced by using a block copolymer having such a side chain structure.

The cationic polyamino acid segment preferably has a positive charge in an approximately equal amount, an approximately half amount, an approximately ¼ amount, or an approximately ⅛ amount, with respect to the negative charge of the nucleic acid included in the unit structure. When the cationic polyamino acid segment has such an electric charge amount, various unit structures having different numbers of contents (for example, one piece, two pieces, four pieces, or eight pieces) of the block copolymer can be obtained.

According to a preferred embodiment, the cationic polyamino acid segment has a positive charge in an amount approximately half the amount of the negative charge of the nucleic acid that is included in the unit structure. It is because when a polyamino acid segment having such a positive charge is formed by an amino acid having one positive charge in the side chain at the blood pH, a unit structure including two block copolymers for one nucleic acid (representatively, a unit structure including two block copolymers and one nucleic acid) is formed, and according to this unit structure, the blood retentivity (consequently, the blood retentivity of the nucleic acid) can be increased. The reason why this effect is provided is not clearly understood; however, for example, it is speculated that when the block copolymer is included at such a ratio, it is made easier for the cationic polyamino acid segments to be disposed across the whole length of the nucleic acid, and as a result, the negative charge of the nucleic acid can be suitably canceled.

The number of amino acid residues included in the cationic polyamino acid segment can be appropriately set according to the electric charge amount desired for the segment. The cationic polyamino acid segment may include non-cationic amino acid residues to the extent that does not impair the effects of the present invention. The number of the non-cationic amino acid residues can be set to, for example, 20% or less, preferably 10% or less, more preferably 5% or less, and even more preferably 2% or less, of the total number of amino acid residues included in the cationic polyamino acid segment.

The hydrophilic polymer chain segment can be formed from an arbitrary appropriate hydrophilic polymer. Examples of the hydrophilic polymer include poly(ethylene glycol), a polysaccharide, poly(vinylpyrrolidone), poly(vinyl alcohol), poly(acrylamide), poly(acrylic acid), poly(methacrylamide), poly(methacrylic acid), a poly(methacrylic acid ester), a poly(acrylic acid ester), a polyamino acid, poly(malic acid), poly(oxazoline), or derivatives of these. Specific examples of the polysaccharide include starch, dextran, fructan, galactan, and the like. Among these, poly(ethylene glycol) can be preferably used, since terminal-reactive polyethylene glycols having various functional groups at the terminals are commercially available, and polyethylene glycols having various molecular weights or branched type polyethylene glycols are commercially available and can be easily obtained.

The length of the hydrophilic polymer chain segment can beset to an appropriate length according to the chain length of the nucleic acid that is included in the unit structure. Specifically, the hydrophilic polymer chain segment is set to be a length that can cover the nucleic acid. According to the present invention, in a case where at least one hydrophilic polymer chain segment in the unit structure has a radius of gyration (Rg) greater than or equal to the length of the nucleic acid (in a case where a plurality of nucleic acids are included, the sum of the lengths of the respective nucleic acids) included in the unit structure, it is considered that the entire nucleic acid is covered by the hydrophilic polymer chain segment. Furthermore, in regard to a unit structure that includes a hydrophilic polymer chain segment disposed so as to have the center of rotation (for example, a linking site to the polyamino acid segment) on one terminal side of the nucleic acid, and a hydrophilic polymer chain segment disposed so as to have the center of rotation on the other terminal side, when the sum of the radii of gyration (Rg) of the hydrophilic polymer chain segments at both ends of the nucleic acid is greater than or equal to the length of the nucleic acid included in the unit structure, it is considered that the entire nucleic acid is covered by the hydrophilic polymer chain segments.

According to a preferred embodiment, the unit structure is composed of one nucleic acid molecule and two block copolymers, and these block copolymers have two chains of PEG as the hydrophilic polymer chain segment at one end of the polyamino acid chain segment. Each of the PEG chains has a molecular weight of preferably 10,000 Da to 80,000 Da, more preferably 20,000 Da to 60,000 Da, and even more preferably 30,000 Da to 45,000 Da.

In regard to the block copolymer described above, the cationic polyamino acid segment and the hydrophilic polymer chain segments are linked by an arbitrary appropriate linking group. The linking group may be an ester bond, an amide bond, an imino group, a carbon-carbon bond, an ether bond, or the like. Furthermore, these segments may also be linked by a linking group that is cleavable in vivo (for example, a disulfide bond, a hydrazone bond, a maleamate bond, or an acetal group). Meanwhile, the cationic polyamino acid-side terminal and/or the hydrophilic polymer chain-side terminal of the block copolymer may be subjected to any arbitrary appropriate modification as long as the effects of the present invention are not adversely affected.

The antitumor agent according to the present invention may constitute a composition together with a pharmaceutically acceptable carrier in accordance with the desired product form, or with other additives and the like. Furthermore, the antitumor agent according to the present invention can be mixed with additives such as an excipient and used in a form that is appropriate for parenteral administration or oral administration.

"Pharmaceutically acceptable" refers to a compound, a material, a composition, and/or a dosage form, which is suitable for a proper advantage/risk ratio to the extent of making right medical judgment, and is appropriate for the use of bringing into contact with human and animal tissues without any problems or complications, such as excessive toxicity, stimulation, and allergic reactions.

A "pharmaceutically acceptable carrier" means a liquid or solid, pharmaceutically acceptable filler, diluent, plastic remedy, solvent, encapsulation material, excipient, or a composition of these, all of which participate in the conveyance or transportation of the antitumor agent according to the present invention to one organ or portion of the body to another organ or portion of the body. Examples of the pharmaceutically acceptable carrier include, for example, sugars such as lactose, glucose, and sucrose; starches such as corn starch and potato starch; cellulose and derivatives thereof, such as carboxymethyl cellulose sodium, ethyl cellulose, and cellulose acetate; tragacanth; gelatin; talc; plastic remedy such as cocoa butter and suppository wax; oils and fats such as peanut oil, cotton seed oil, safflower oil, sesame oil, olive oil, corn oil, and soybean oil; glycols such as ethylene glycol and propylene glycol; polyols such as glycerin, sorbitol, mannitol, polyethylene glycol, and polypropylene glycol; esters such as ethyl oleate and ethyl laurate; agar-agar; buffering agents such as magnesium hydroxide and aluminum hydroxide; alginic acid; pyrogen-free water; an isotonic sodium chloride solution; Ringer's solution; ethyl alcohol; buffer solutions such as phosphate buffer solution; and the like.

In addition to those, a wetting agent, an emulsifier, a lubricating agent, a colorant, a releasing agent, a coating agent, a sweetener, a flavoring agent, a fragrance, a preservative, and an oxidation inhibitor may also exist in the antitumor agent.

Examples of a pharmaceutically acceptable oxidation inhibitor include the following: water-soluble oxidation inhibitors such as ascorbic acid, cysteine hydrochloride, sodium hydrogen sulfate, sodium disulfite, and sodium sulfite; oil-soluble oxidation inhibitors such as ascorbyl palmitate, butyl hydroxyanisole (BHA), butyl hydroxytoluene (BHT), lecithin, propyl gallate, and α-tocopherol; and metal chelating agents such as citric acid, ethylenediaminetetraacetic acid (EDTA), sorbitol, tartaric acid, and phosphoric acid, can also be incorporated as necessary.

An antitumor agent that has been formulated in a form suitable for parenteral administration can include, together with the compound according to the present invention, one or a plurality of pharmaceutically acceptable solvents, dispersants, emulsifiers, oxidation inhibitors, buffer agents, bacteriostatic agents, isotonizing agents, and/or suspending agents. In the case of formulating for parenteral administration, the compound according to the present invention can be formulated as an aqueous solution, a non-aqueous solution, a suspension, liposomes, or an emulsion, in which the compound is used in appropriate combination with purified water, an appropriate buffer solution such as a phosphate buffer solution; a physiological alt solution such as physiological saline, Ringer's solution (Ringer's solution), or Locke's solution; ethanol, glycerin, surfactant, and the like. Preferably, the compound is formulated as a sterilized aqueous solution for injection and is administered intravenously, intraperitoneally, subcutaneously, intramuscularly, or the like. At this time, it is preferable that the preparation has a physiologically pH, and preferably pH in the range of 6 to 8. Furthermore, the compound may also be administered transdermally to a target site and peripheral sites thereof as a liquid preparation such as a lotion, a suspension, or an emulsion; a semi-solid preparation such as a gel, a cream, or an ointment; a powdered drug, a powder (powder-like), a solid preparation for prior preparation, or as an external agent such as a patch. Furthermore, the compound can also be administered as a suppository using a base agent for suppository. Among those described above, a preferable preparation, dosage form, and the like can be selected by the physician in charge. A semi-solid preparation such as a lotion, a cream, or an ointment is obtained by appropriately mixing the compound according to the present invention with one or more selected from the group consisting of fats, fatty oil, lanolin, petrolatum, paraffin, wax, plaster, resins, plastics, glycols, higher alcohols, glycerin, water, emulsifiers, suspending agents, and the like.

The antitumor agent can also include adjuvants such as a preservative, a wetting agent, an emulsifier, and a dispersant; for example, various antibacterial agents and antifungal agents, such as parabens, chlorobutanol, and phenol sorbate; sugars; and isotonic agents such as sodium chloride. Furthermore, by using an active material that delays absorption, such as aluminum monostearate and gelatin, the absorption sustaining properties of the preparation can also be adjusted.

The amount of administration of the antitumor agent according to the present invention varies depending on the object disease, the object of administration, the administration route, or the like. For example, since the dose can be easily varied depending on the conditions such as the body weight of the person to be treated, the amount of administration can be selected as appropriate by those ordinarily skilled in the art; however, it is desirable that the amount of administration in terms of the active ingredient is, for example, in the range of 0.001 to 1,000 mg/day/kg of body weight, and in the range of 0.01 to 100 mg/day/kg of body weight.

The antitumor agent according to the present invention may be used in combination with other antitumor agents as necessary. Examples of the other antitumor agents include fluorouracil, tegafur, a tegafur-uracil combination drug, a tegafur-gimeracil-oteracil potassium combination drug, doxifluridine, capecitabine, carmofur, cytarabine, citarabine ocfosfate, enocitabine, gemcitabine, azacitidine, decitabine, floxuridine, ethynylcytidine, 6-mercaptopurine, fludarabine, pentostatin, nelarabine, 6-thioguanine, cladribine, clofarabine, methotrexate, pemetrexed, raltitrexed, nolatrexed, pralatrexate, trimetrexate, idatrexate, hydroxycarbamide, cisplatin, carboplatin, nedaplatin, oxaliplatin, satraplatin, miriplatin, lobaplatin, spiroplatin, tetraplatin, ormaplatin, iproplatin, cyclophosphamide, ifosfamide, busulfan, melphalan, nitrogen mustard, chlorambucil, glufosfamide, mafosfamide, estramustine, nimustine, lanimustine, carmustine, lomustine, semustine, streptozocin, procarbazine, dacarbazine, temozolomide, thiotepa, hexamethylmelamine, trabectedin, apaziquone, altretamine, bendamustine, mitolactol, anthracycline-based antibiotics (for example, doxorubicin, daunorubicin, pirarubicin, epirubicin, idarubicin, aclarubicin, amrubicin, zorubicin, valrubicin, liposomal doxorubicin, pixantrone, and mitoxantrone), mitomycin C, bleomycin, peplomycin, actinomycinD, zinostatinstimalamer, topotecan, irinotecan, exatecan, nogitecan, etoposide, teniposide, sobuzoxane, vincristine, vinblastine, vindesine, vinorelbine, vinflunine, monomethyl auristatin E, epothilone B, eribulin, paclitaxel, docetaxel, cabazitaxel, tamoxifen, toremifene, raloxifene, fulvestrant, anastrozole, exemestane, letrozole, aminoglutethimide, formestane, vorozole, methyltestosterone, medroxyprogesterone, megestrol, gestonorone, mepithiostan, flutamide, nilutamide, bicalutamide, finasteride, chlormadinone, estramustine, diethylstilbestrol, ethinyl estradiol, fosfestrol, polyestradiol phosphate, prednisolone, dexamethasone, mitotane, goserelin, leuprorelin, buserelin, triptorelin, bevacizumab, aflibercept, MV833, cetuximab, pegaptanib, pazopanib, CBO-P11, sunitinib, sorafenib, ranibizumab, vatalanib, axitinib, zactima, NX1838, angiozyme, semaxanib, lestaurtinib, TSU-68, ZD4190, temsirolimus, angiostatin, endostatin, TNP-470, CP-547632, CPE-7055, KRN633, AEE788, IMC-1211B, PTC-299, E7820, lenvatinib, marimastat, neovastat, purinomastat, metastat, BMS-275291, MMI270, S-3304, vitaxin, carboxyamidotriazole orotate, thalidomide, genistein, interferon α, interleukin 12, and the like.

EXAMPLES

The effects of the present invention will be described using the following Examples and Comparative Examples. However, the technical scope of the present invention is not intended to be limited to the following Examples only.

Test Example 1

Syn-1

A double-stranded nucleic acid molecule (Syn-1) having a first polynucleotide chain represented by the following SEQ ID NO:3 and a second polynucleotide chain represented by the following SEQ ID NO:4 was prepared, and the activity of suppressing the proliferation of urinary bladder cancer cells (JB-V235 cells) was evaluated. Meanwhile, in the following SEQ ID NO: 3, the two residues (GG) on the 3'-terminal side is a 3'-terminal addition sequence, and the other portion corresponds to a complementarity region. Furthermore, in the following SEQ ID NO: 4, the two residues (GG) on the 3'-terminal side is a 3'-terminal addition sequence, and the other portion corresponds to a hybridization region.

```
SEQ ID NO: 3:
5'-AGGGAUUCCUGGGAAAACUGGACGG-3'

SEQ ID NO: 4:
5'-GUCCAGUUUUCCCAGGAAUCCCUGG-3'
```

A conventional miR-145 analogue (A-miR-145) was purchased from Life Technologies Corporation and used.

JB-V235 cells (human urinary bladder cancer cells) were obtained from Human Science Resource Bank (HSRRB, Human Science Promotion Foundation), and the cells were cultured in an incubator (air/$CO_2$=95/5 (v/v)) at 37° C. using RPMI164 medium (10% (v/v) fetal calf serum (FCS) added).

JB-V235 cells were inoculated onto a 6-well plate at a concentration of $5\times10^4$ to $6\times10^4$ cells/ml, and the next day, the cells were transfected with Syn-1 as described above or A-miR-145 (all at a final concentration of 10 nM). Meanwhile, transfection was carried out by using cationic liposomes (Lipofectamine (registered trademark) RNAiMAX, Life Technologies Corp.) according to the manufacturer's protocol.

The time point immediately after the transfection was designated as zero (0) hour, subsequently culturing was carried out up to 72 hours, and the viable cell count was measured by the Trypan blue staining method. As a negative control plot (Cont), a control miRNA purchased from Dharmacon, Inc. was used, and viable cells (%) were calculated as a relative cell count in the case where the viable cell count in the negative control plot was designated as 100%. The results are shown in FIG. 1 (*: $p<0.05$). Meanwhile, regarding a statistical analysis, the statistical significance was evaluated by a two-tailed Student's t-test using a GraphPad Prism Software system (GraphPad Software, Inc.). The value is indicated as the average±standard deviation obtained by evaluating cells from 6 to 12 wells.

As shown in the FIG. 1, in both cases of Syn-1 of the present invention and A-miR-145, the viable cell count was reduced compared to the control plot. With Syn-1, the viable cell count was significantly reduced, even when compared with A-miR-145, which is an analogue of conventional miR-145.

(Western Blotting: JB-V235 Cells)

Syn-1 or A-miR-145 (all at a final concentration of 5 nM) was transfected into JB-V235 cells by the same procedures described above. The cells were harvested with a cell scraper after 72 hours from the transfection, and the amounts of expression of cancer-related molecules (c-Myc and Fascin) were analyzed by the following Western Blotting.

More specifically, the cells were homogenized in an ice-cooled lysis buffer (10 mM Tris-HCl (pH 7.4), 1% (w/v) NP-40, 0.1% (w/v) deoxycholic acid, 0.1% (w/v) SDS, 150 mM NaCl, 1 mM EDTA, and 1% (w/v) Protease Inhibitor Cocktail (Sigma-Aldrich Corporation), and the cells were left to stand on ice for 20 minutes. The homogenate was centrifuged for 20 minutes (4° C.) at 13,000 rpm, and then the supernatant was collected as a sample for Western Blotting. The protein content in the sample was measured using a DC Protein Assay Kit (manufactured by Bio-Rad Laboratories, Inc.). The sample (amount equivalent to 10 μg of proteins) was separated by SDS-PAGE using a 10.0 or 12.5% (w/v) polyacrylamide gel and was transferred onto a PVDF membrane (Perkin Elmer Life Sciences, Inc.). The sample was incubated for one hour in PBS (PBS-T) including a 5% (w/v) defatted emulsion (produced with PBS (PBS-T) including 0.1% (w/v) Tween (registered trademark)), and non-specific bonds were blocked. Subsequently, the membrane was incubated overnight at 4° C. together with primary antibodies (anti-c-Myc antibody (Santa Cruz Biotechnology, Inc.) and anti-Fascin antibody (Cell Signaling Technology, Inc.)) that had been adequately diluted with a PBS-T including 2% (w/v) bovine serum albumin and 0.01% (w/v) sodium azide. Next, the membrane was washed three times with PBS-T and was further incubated at room temperature together with a secondary antibody (HRP-bound anti-rabbit or anti-mouse IgG antibody, Cell Signaling Technology, Inc.). Next, the membrane was washed three times with PBS-T. The immunoblot was visualized using Amersham ECL Plus Western Blotting Detection Reagent (GE Healthcare Systems). β-Actin was used as the internal standard by re-incubating the same membrane using anti-β-Actin antibody (Sigma-Aldrich Corporation).

Figure 2:
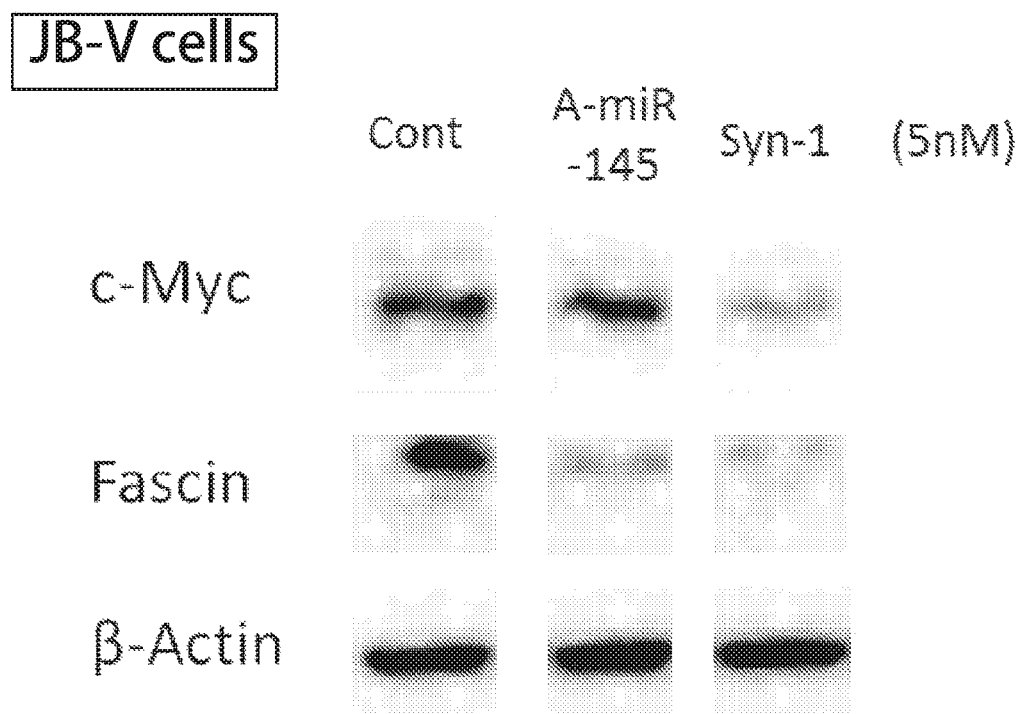
FIG. 2 shows the results of analyzing the amount of protein expression of cancer-related molecules (c-Myc and Fascin) using JB-V235 cells in Test Example 1.

The results for the Western Blotting are shown in FIG. 2. As shown in the FIG. 2, the amounts of expression of c-Myc and Fascin were markedly decreased by the transfection with Syn-1.

Subsequently, Syn-1 or A-miR-145 was transfected into T-24 cells, which are human urinary bladder cancer cells. Meanwhile, T-24 cells were purchased from Human Science Resource Bank (HSRRB, Human Science Promotion Foundation) and were cultured in an incubator (air/$CO_2$=95/5 (v/v)) at 37° C. using RPMI164 medium (10% (v/v) fetal calf serum (FCS) added).

Regarding the transfection operation, specifically, T-24 cells were inoculated onto a 6-well plate at a concentration of $0.5 \times 10^5$ to $1 \times 10^5$ cells/ml, and the next day, the above-mentioned Syn-1 or A-miR-145 (all at a final concentration of 10 nM) was transfected. Meanwhile, the transfection was carried out by using cationic liposomes (Lipofectamine (registered trademark) RNAiMAX, Life Technologies Corp.) according to the manufacturer's protocol.

Figure 3:
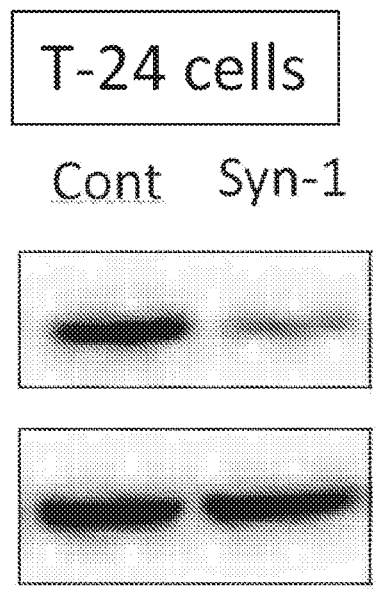
FIG. 3 shows the results of analyzing the amount of protein expression of a cancer-related molecule (Fascin) using T-24 cells in Test Example 1.

The time point immediately after the transfection was designated as zero (0) hour, and then culturing was carried out up to 72 hours. At this time, as a negative control plot (Cont), a control miRNA purchased from Dharmacon, Inc. was used. Next, the cells were harvested with a cell scraper after culturing, Western Blotting was performed by the same procedures described above, and the amount of expression of a cancer-related molecule (Fascin) was analyzed. The results of the Western Blotting are shown in FIG. 3. As shown in the FIG. 3, the amount of expression of Fascin was markedly decreased by the transfection of Syn-1.

Test Example 2

Syn-2

A double-stranded nucleic acid molecule (Syn-2) having a first polynucleotide chain represented by SEQ ID NO:3 described above and a second polynucleotide chain represented by the following SEQ ID NO:5 was prepared. Meanwhile, in the following SEQ ID NO:5, the two residues (TT) on the 3'-terminal side is a 3'-terminal addition sequence, and the other portion corresponds to a hybridization region.

```
SEQ ID NO: 5:
5'-GUCCAGUUUUCCCAGGAAUCCCUTT-3'
```

Syn-3

A double-stranded nucleic acid molecule (Syn-3) having a first polynucleotide chain represented by the following SEQ ID NO:6 and a second polynucleotide represented by the above-described SEQ ID NO:4 was prepared. Meanwhile, in the following SEQ ID NO: 6, the two residues (TT) on the 3'-terminal side is a 3'-terminal addition sequence, and the other portion corresponds to a complementarity region.

```
SEQ ID NO: 6:
5'-AGGGAUUCCUGGGAAAACUGGACTT-3'
```

By using the Syn-1, Syn-2, and Syn-3 described above, the activity of suppressing the proliferation of urinary bladder cancer cells (T-24 cells) was evaluated according to the method described below. In the following Table 1, the correspondence relations between the first polynucleotide chain and the second polynucleotide chain in the respective double-stranded nucleic acid molecules are shown. As shown in the following Table 1, in the double-stranded nucleic acid molecules (Syn-1, Syn-2, and Syn-3) according to the present invention, the nucleotide sequence of the first polynucleotide chain and the nucleotide sequence of the second polynucleotide chain, except for the 3'-terminal addition sequences, are in a complementary relationship.

TABLE 1

```
Syn-1  Second polynucleotide  SEQ ID NO: 4   5'-  G U C C A G U U U U C C C A G G A A U C C C U G G-3'
       chain                                      | | | | | | | | | | | | | | | | | | | | | | |
       First polynucleotide   SEQ ID NO: 3   3'-G G C A G G U C A A A A G G G U C C U U A G G G A    -5'
       chain
```

TABLE 1-continued

```
Syn-2   Second polynucleotide   SEQ ID NO: 5   5'-    G U C C A G U U U U C C C A G G A A U C C C U T T-3'
        chain                                          | | | | | | | | | | | | | | | | | | | | |
        First polynucleotide    SEQ ID NO: 3   3'-G G C A G G U C A A A A G G G U C C U U A G G G A    -5'
        chain Syn-3   Second polynucleotide   SEQ ID NO: 4   5'-    G U C C A G U U U U C C C A G G A A U C C C U G G-3'
        chain                                          | | | | | | | | | | | | | | | | | | | | |
        First polynucleotide    SEQ ID NO: 6   3'-T T C A G G U C A A A A G G G U C C U U A G G G A    -5'
        chain hsa-    Guide strand            SEQ ID NO: 8              U C         U     C
miR-    (hsa-miR-145-5p)                       5'-    G      C A G U   U U   C C A G G A A U C C C U    -3'
145                                                   |      | | | |   | |   | | | | | | | | | | |
                                SEQ ID NO: 7   3'-U U C      G U C A   A A   G G U C C U U A G G       -5'
                                                      U U              U     A
```

(In the above table, the symbol "|" represents the site of complementary bases between the two polynucleotide strands.)

T-24 cells (human urinary bladder cancer cells) were purchased from Human Science Resource Bank (HSRRB, Human Science Promotion Foundation) and were cultured in an incubator (air/$CO_2$=95/5 (v/v)) at 37° C. using RPMI164 medium (10% (v/v) fetal calf serum (FCS) added).

Transfection of the double-stranded nucleic acid molecules was carried out by the same procedures as the Test Example 1, and thereafter, the cells were cultured for 72 hours. The viable cell counts were measured. The results are shown in FIG. 4.

Figure 4:
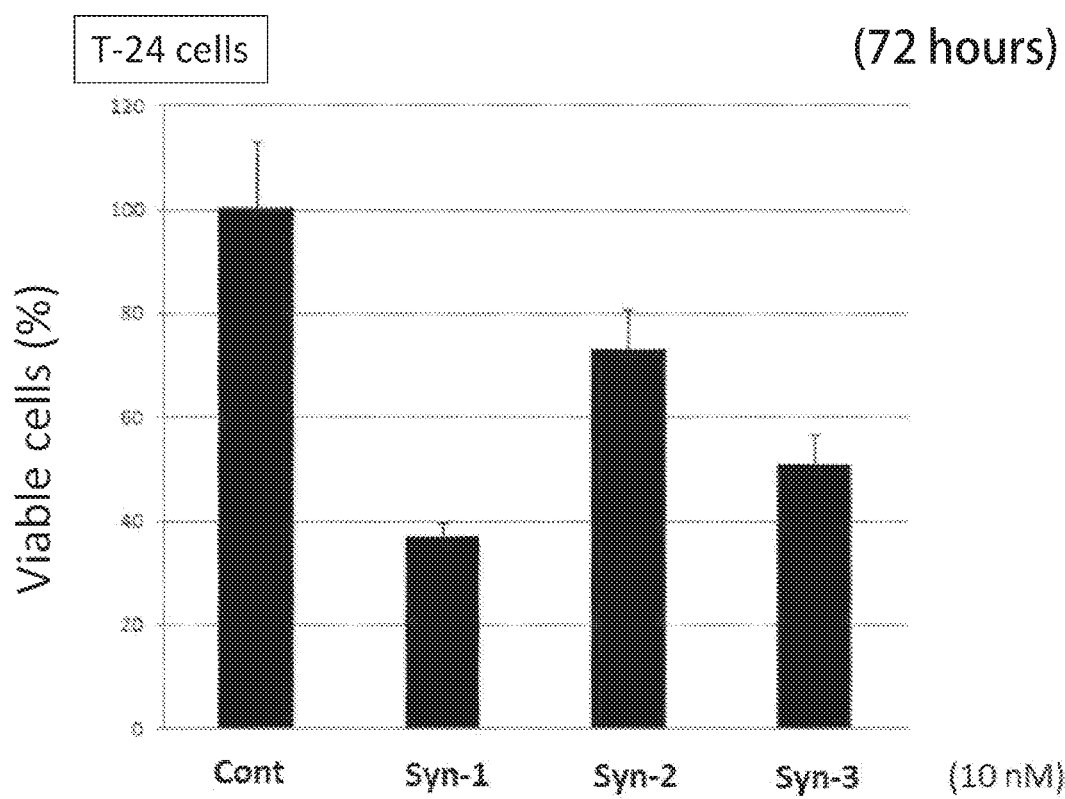
FIG. 4 shows the results of an evaluation of the viable cell count in Test Example 2.

As shown in the FIG. 4, for all of the Syn-1, Syn-2, and Syn-3 of the present invention, the viable cell count was decreased compared to the control plot. Furthermore, in the Syn-1, the viable cell count was particularly decreased.

Test Example 3

The activity of suppressing the proliferation of colon cancer cells (DLD-1 cells) was evaluated using the Syn-1, Syn-2, and Syn-3 described above.

DLD-1 cells (human colon cancer cells) were purchased from Human Science Resource Bank (HSRRB, Human Science Promotion Foundation) and were cultured in an incubator (air/$CO_2$=95/5 (v/v)) at 37° C. using RPMI164 medium (10% (v/v) fetal calf serum (FCS) added).

Transfection of the double-stranded nucleic acid molecules was performed by the same procedures as the Test Example 1, and thereafter, the cells were cultured for 72 hours. The viable cell counts were measured. The results are shown in FIG. 5.

Figure 5:
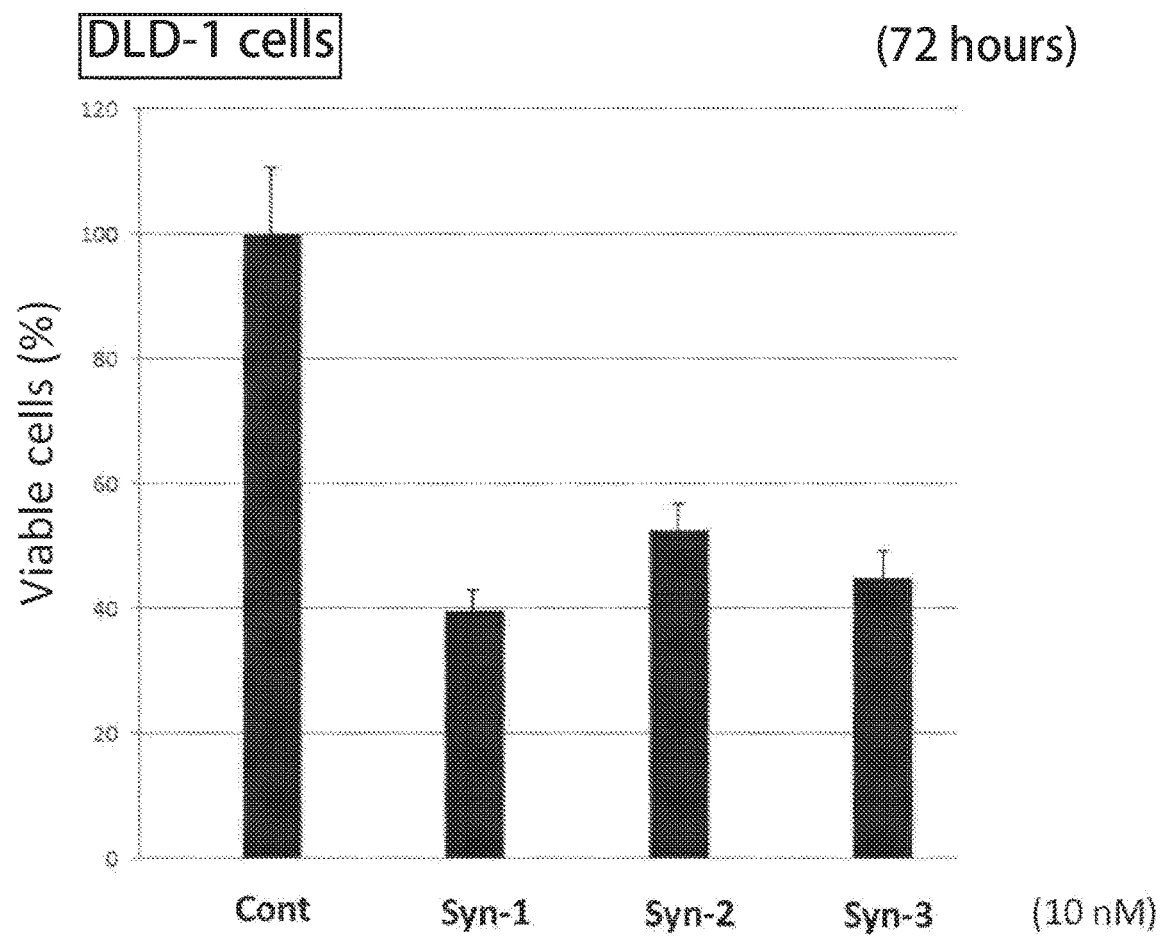
FIG. 5 shows the results of an evaluation of the viable cell count in Test Example 3.

As shown in the FIG. 5, for all of the Syn-1, Syn-2, and Syn-3 of the present invention, the viable cell count was decreased compared to the control plot. Furthermore, in the Syn-1, the viable cell count was particularly decreased.

Test Example 4

By using the Syn-1 and A-miR-145, T-24 cells were transfected to a final concentration of 5 nM, 10 nM, or 15 nM. After 72 hours from the transfection, the viable cell counts were measured in the same manner as in the Test Example 1. The results are shown in FIG. 6.

Figure 6:
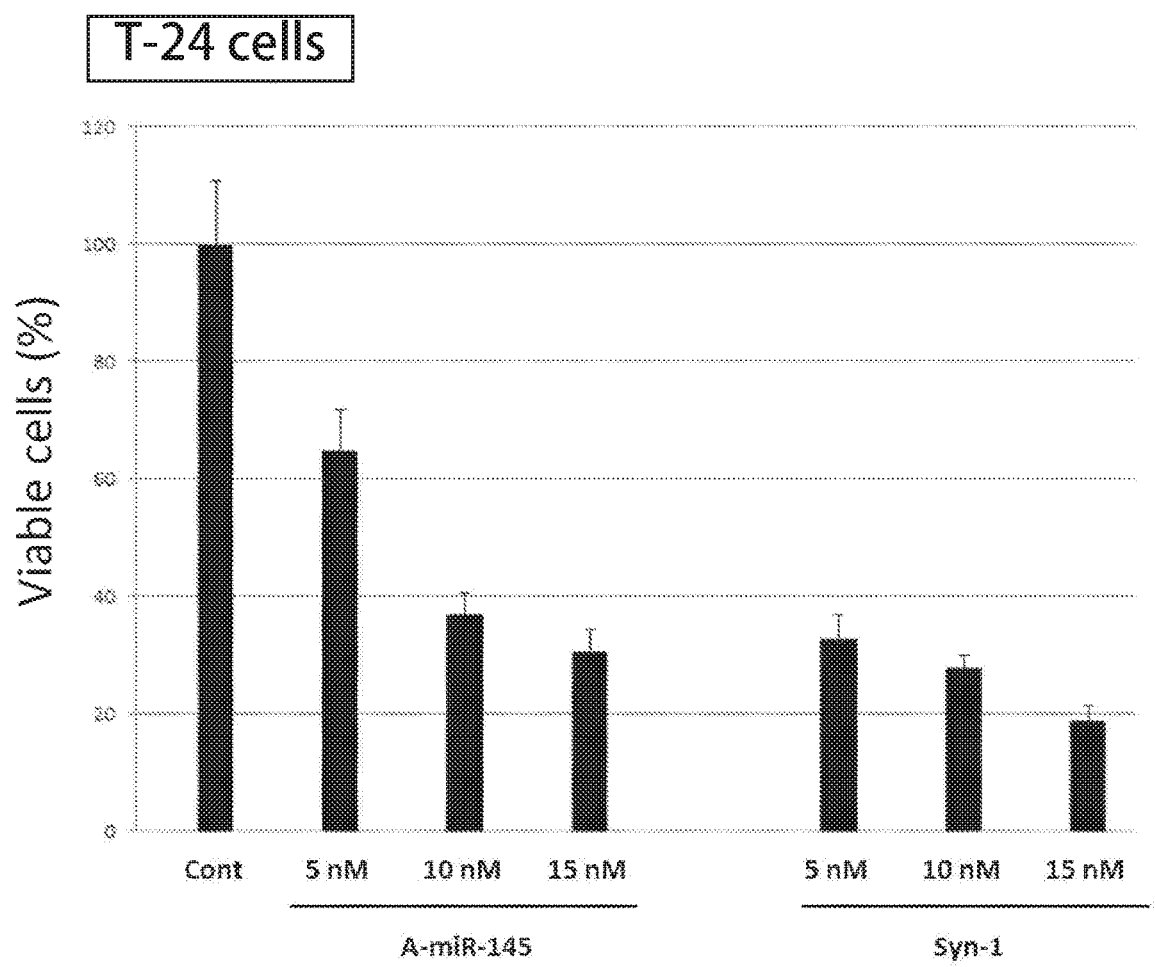
FIG. 6 shows the results of an evaluation of the viable cell count in Test Example 4.

As shown in the FIG. 6, Syn-1 suppressed the proliferation of cancer cells in a concentration-dependent manner.

Test Example 5

Syn-4

A double-stranded nucleic acid molecule (Syn-4) having a first polynucleotide chain represented by SEQ ID NO:3 described above and a second polynucleotide chain represented by the following SEQ ID NO:9 was prepared. Meanwhile, in the following SEQ ID NO:9, the two residues (TT) on the 3'-terminal side is a 3'-terminal addition sequence, and the other portion corresponds to a hybridization region. Furthermore, the phosphodiester bond at the four sites represented by the symbol "^" in SEQ ID NO: 9 was substituted by a phosphorothioate bond. Furthermore, the underlined bases in SEQ ID NO:9 included a modified sugar moiety of 2'-fluoro, and the double-underlined bases included a modified sugar moiety of 2'-O-methyl.

SEQ ID NO: 9
5'-G^U^CCAGUUUCCCAGGAAUCCCU^T^T-3'

Syn-5

A double-stranded nucleic acid molecule (Syn-5) having a first polynucleotide chain represented by the following SEQ ID NO:10 and a second polynucleotide chain represented by SEQ ID NO:4 described above was prepared. Meanwhile, in the following SEQ ID NO:10, the two residues (TT) on the 3'-terminal side is a 3'-terminal addition sequence, and the other portion corresponds to a complementarity region. Furthermore, the phosphodiester bond at the four sites represented by the symbol "^" in SEQ ID NO: 10 was substituted by a phosphorothioate bond. Furthermore, the underlined bases in SEQ ID NO:10 included a modified sugar moiety of 2'-fluoro, and the double-underlined bases included a modified sugar moiety of 2'-O-methyl.

SEQ ID NO: 10:
5'-A^G^GGAUUCCUGGGAAAACUGGAC^T^T-3'

Syn-6

A double-stranded nucleic acid molecule (Syn-6) having a first polynucleotide chain represented by SEQ ID NO:3 described above and a second polynucleotide chain represented by the following SEQ ID NO:11 was prepared. Meanwhile, in the following SEQ ID NO:11, the two residues (TT) on the 3'-terminal side is a 3'-terminal addition sequence, and the other portion corresponds to a hybridization region. Furthermore, the phosphodiester bond at the four sites represented by the symbol "^" in SEQ ID NO: 11 was substituted by a phosphorothioate bond. Furthermore, the underlined bases in SEQ ID NO:11 included a modified sugar moiety of 2'-fluoro, and the double-underlined bases included a modified sugar moiety of 2'-O-methyl.

SEQ ID NO: 11:
5'-G^U^CCAGUUUCCCAGGAAUCCCU^T^T-3'

Syn-7

A double-stranded nucleic acid molecule (Syn-7) having a first polynucleotide chain represented by the following SEQ ID NO:12 and a second polynucleotide chain represented by SEQ ID NO:4 described above was prepared. Meanwhile, in the following SEQ ID NO:12, the two residues (TT) on the 3'-terminal side is a 3'-terminal addition sequence, and the other portion corresponds to a complementarity region. Furthermore, the phosphodiester bond at the four sites represented by the symbol "^" in SEQ ID NO: 12 was substituted by a phosphorothioate bond. Furthermore, the underlined bases in SEQ ID NO:12 included a modified sugar moiety of 2'-fluoro, and the double-underlined bases included a modified sugar moiety of 2'-O-methyl.

SEQ ID NO: 12:
5'-A^G^GGAUUCCUGGGAAAACUGGAC^T^T-3'

By using the Syn-1 and Syn-4 to Syn-7 described above, the activity of suppressing the proliferation of urinary bladder cancer cells (T-24 cells) was evaluated according to the same procedures as the Test Example 2 described above. In the following Table 2, the correspondence relations between the first polynucleotide chain and the second polynucleotide chain in the respective double-stranded nucleic acid molecules are shown. As shown in the following Table 2, in the double-stranded nucleic acid molecules (Syn-1 and Syn-4 to Syn-7) according to the present invention, the nucleotide sequence of the first polynucleotide chain and the nucleotide sequence of the second polynucleotide chain, except for the 3'-terminal addition sequences, are in a complementary relationship.

TABLE 2

```
Syn-1  Second polynucleotide  SEQ ID NO: 4   5'-     G U C C A G U U U U C C C A G G A A U C C C U G G-3'
       chain                                          | | | | | | | | | | | | | | | | | | | | | |
       First polynucleotide   SEQ ID NO: 3   3'-G G C A G G U C A A A A G G G U C C U U A G G G A      -5'
       chain Syn-4  Second polynucleotide  SEQ ID NO: 9   5'-     G^U^C C A G U U U U C C C A G G A A U C C C U^T^T-3'
       chain                                          | | | | | | | | | | | | | | | | | | | | | |
       First polynucleotide   SEQ ID NO: 3   3'-G G C A G G U C A A A A G G G U C C U U A G G G A      -5'
       chain Syn-5  Second polynucleotide  SEQ ID NO: 4   5'-     G U C C A G U U U U C C C A G G A A U C C C U G G-3'
       chain                                          | | | | | | | | | | | | | | | | | | | | | |
       First polynucleotide   SEQ ID NO: 10  3'-T^T^C A G G U C A A A A G G G U C C U U A G G^G^A      -5'
       chain Syn-6  Second polynucleotide  SEQ ID NO: 11  5'-     G U C C A G U U U U C C C A G G A A U C C C U^T^T-3'
       chain                                          | | | | | | | | | | | | | | | | | | | | | |
       First polynucleotide   SEQ ID NO: 3   3'-G G C A G G U C A A A A G G G U C C U U A G G G A      -5'
       chain Syn-7  Second polynucleotide  SEQ ID NO: 4   5'-     G U C C A G U U U U C C C A G G A A U C C C U G G-3'
       chain                                          | | | | | | | | | | | | | | | | | | | | | |
       First polynucleotide   SEQ ID NO: 12  3'-T^T^C A G G U C A A A A G G G U C C U U A G G^G^A      -5'
       chain
```

(In the above table, the symbol "|" represents the site of complementary bases between the two polynucleotide strands, and the symbol "^" means that a phosphodiester bond is substituted by a phosphorothioate bond. Underline and double underline mean that the bases include a 2'-fluoro modified sugar moiety and a 2'-O-methyl modified sugar moiety, respectively.)

The results of the proliferation suppressing activity test described above are shown in FIG. 7.

Figure 7:
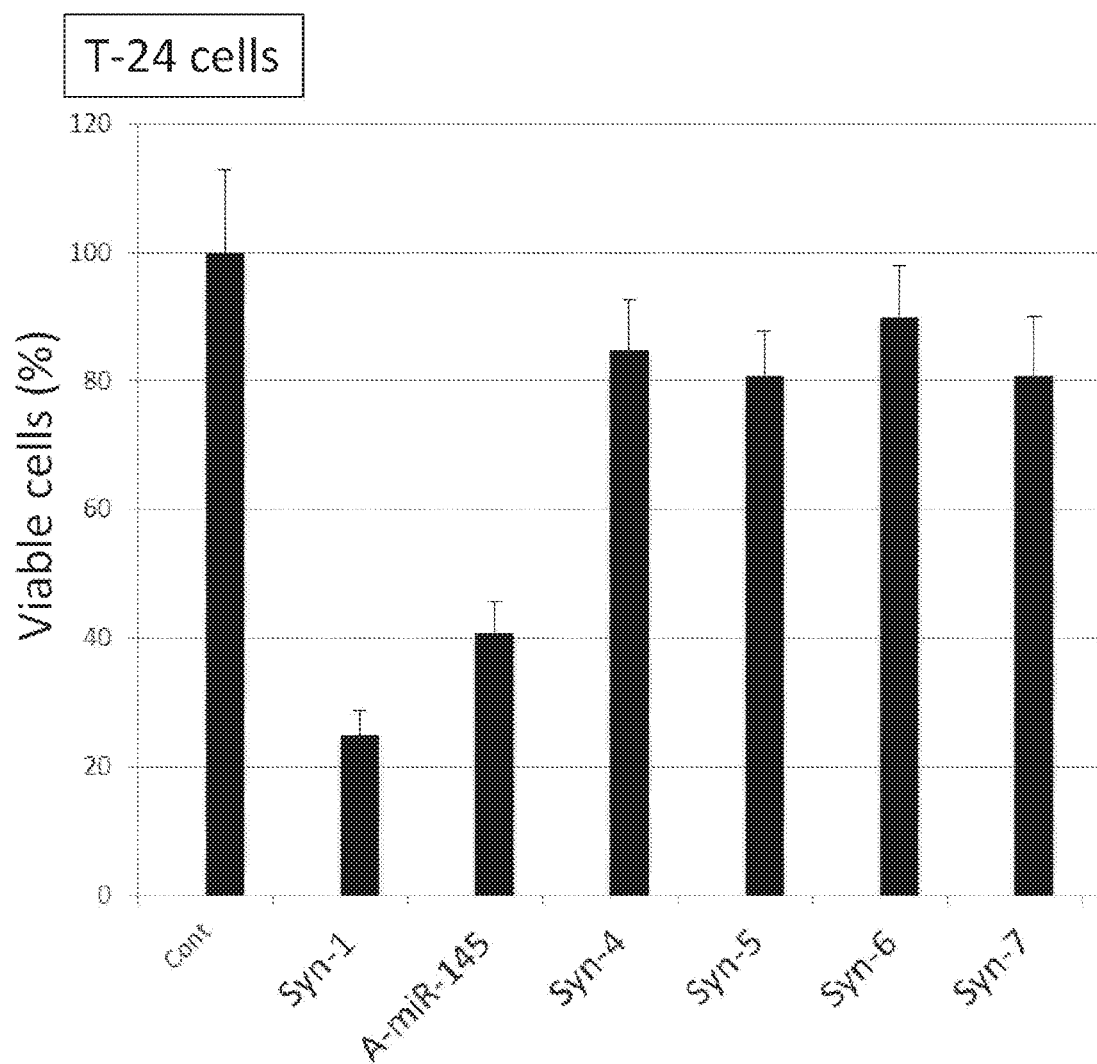
FIG. 7 shows the results of an evaluation of the viable cell count in Test Example 5.

As shown in the FIG. 7, for all of the Syn-1 and Syn-4 to Syn-7 of the present invention, the viable cell count was decreased compared to the control plot. Furthermore, in the Syn-1, the viable cell count was particularly decreased.

Test Example 6

Syn-8

A double-stranded nucleic acid molecule (Syn-8) having a first polynucleotide chain represented by the following SEQ ID NO:13 and a second polynucleotide chain represented by SEQ ID NO:4 described above was prepared. Meanwhile, in the following SEQ ID NO:13, a 3'-terminal addition sequence does not exist on the 3'-terminal side.

```
SEQ ID NO: 13:
5'-AGGGAUUCCUGGGAAAACUGGAC-3'
```

Syn-9

A double-stranded nucleic acid molecule (Syn-9) having a first polynucleotide chain represented by the following SEQ ID NO:14 and a second polynucleotide chain represented by the following SEQ ID NO:15 was prepared. Meanwhile, the structure of the first polynucleotide represented by SEQ ID NO:14 corresponds to a structure in which a structure represented by the Chemical Formula (3) described above (a hydroxyl group is bonded to *2; benzenepyridine (BP) structure) was added to the 3'-terminal of the polynucleotide represented by SEQ ID NO:13. Furthermore, the structure of the second polynucleotide represented by SEQ ID NO:15 corresponds to a structure in which the 3'-terminal addition sequence (GG) of the polynucleotide represented by SEQ ID NO:4 was substituted by a structure represented by the Chemical Formula (3) described above (a hydroxyl group is bonded to *2; benzenepyridine (BP) structure).

```
SEQ ID NO: 14:
5'-AGGGAUUCCUGGGAAAACUGGAC-BP-3'

SEQ ID NO: 15:
5'-GUCCAGUUUUCCCAGGAAUCCCU-BP-3'
```

Syn-10

A double-stranded nucleic acid molecule (Syn-10) having a first polynucleotide chain represented by SEQ ID NO:3 described above (having a 3'-terminal addition sequence (GG)) and a second polynucleotide chain represented by SEQ ID NO: 15 described above (having a BP structure at the 3'-terminal) was prepared.

Syn-11

A double-stranded nucleic acid molecule (Syn-11) having a first polynucleotide chain represented by SEQ ID NO:13 described above (not having a 3'-terminal addition sequence) and a second polynucleotide chain represented by SEQ ID NO: 15 described above (having a BP structure at the 3'-terminal) was prepared.

Syn-12

A double-stranded nucleic acid molecule (Syn-12) having a first polynucleotide chain represented by the following SEQ ID NO:16 and a second polynucleotide chain represented by SEQ ID NO:8 described above (hsa-miR-145-5p) was prepared. Meanwhile, in the following SEQ ID NO:16, the two residues (UU) on the 3'-terminal side is a 3'-terminal addition sequence, and the other portion corresponds to a complementarity region. Furthermore, the phosphodiester bond at the four sites represented by the symbol "A" in SEQ ID NO:16 was substituted by a phosphorothioate bond. Furthermore, the underlined bases in SEQ ID NO:16 included a modified sugar moiety of 2'-fluoro, and the double-underlined bases included a modified sugar moiety of 2'-O-methyl.

```
SEQ ID NO: 16:
5'-G^G^AUUCCUGGAAAUACUGGUUC^U^U-3'
```

In the following Table 3, the correspondence relations between the first polynucleotide chain and the second polynucleotide chain in the respective double-stranded nucleic acid molecules are shown. As shown in the following Table 3, in the double-stranded nucleic acid molecules (Syn-1 and Syn-8 to Syn-11) according to the present invention, the nucleotide sequence of the first polynucleotide chain and the nucleotide sequence of the second polynucleotide chain, except for the 3'-terminal addition sequences, are in a complementary relationship. On the other hand, in the Syn-12 having a base sequence that is identical to wild type miR-145, mismatch exists at four sites other than the 3'-terminal addition sequence.

TABLE 3

| | | | |
|---|---|---|---|
| Syn-1 | Second polynucleotide chain | SEQ ID NO: 4 | 5'- G U C C A G U U U U C C C A G G A A U C C C U G G-3' |
| | | | \|\|\|\|\|\|\|\|\|\|\|\|\|\|\|\|\|\|\|\|\|\| |
| | First polynucleotide chain | SEQ ID NO: 3 | 3'-G G C A G G U C A A A A G G G U C C U U A G G G A    -5' |
| Syn-8 | Second polynucleotide chain | SEQ ID NO: 4 | 5'- G U C C A G U U U U C C C A G G A A U C C C U G G-3' |
| | | | \|\|\|\|\|\|\|\|\|\|\|\|\|\|\|\|\|\|\|\|\|\| |
| | First polynucleotide chain | SEQ ID NO: 13 | 3'-    C A G G U C A A A A G G G U C C U U A G G G A    -5' |
| Syn-9 | Second polynucleotide chain | SEQ ID NO: 15 | 5'- G U C C A G U U U U C C C A G G A A U C C C U Bp -3' |
| | | | \|\|\|\|\|\|\|\|\|\|\|\|\|\|\|\|\|\|\|\|\|\| |
| | First polynucleotide chain | SEQ ID NO: 14 | 3'-Bp C A G G U C A A A A G G G U C C U U A G G G A    -5' |
| Syn-10 | Second polynucleotide chain | SEQ ID NO: 15 | 5'- G U C C A G U U U U C C C A G G A A U C C C U Bp -3' |
| | | | \|\|\|\|\|\|\|\|\|\|\|\|\|\|\|\|\|\|\|\|\|\| |
| | First polynucleotide chain | SEQ ID NO: 3 | 3'-G G C A G G U C A A A A G G G U C C U U A G G G A    -5' |

TABLE 3-continued

```
Syn-11  Second polynucle-          SEQ ID NO: 15  5'-   G U C C A G U U U U C C C A G G A A U C C C U Bp -
        otide chain                               3'
                                                        | | | | | | | | | | | | | | | | | | | | |
        First polynucleotide chain SEQ ID NO: 13  3'-   C A G G U C A A A A G G G U C C U U A G G G A    -
                                                   5'

Syn-12  Second polynucle-          SEQ ID NO: 8         U C           U         C
        otide chain
        (hsa-miR-145-5p)                          5'-  G      C A G U   U U   C C A G G A A U C C C U   -
                                                  3'
                                                        |      | | | |   | |   | | | | | | | | | |
        First polynucleotide chain SEQ ID NO: 16 3'-U^U^C     G U C A   A A   G G U C C U U A^G^
                                                       G     -5'
                                                       ‗      U U           U     A
                                                              ‗ ‗           ‗     ‗
```

(In the above table, the symbol "|" represents the site of complementary bases between the two polynucleotide strands, and the symbol "^" means that a phosphodiester bond is substituted by a phosphorothioate bond. Underline and double underline mean that the bases include a 2'-fluoro modified sugar moiety and a 2'-O-methyl modified sugar moiety, respectively.)

By using the Syn-1 and Syn-8 to Syn-11 described above, the activity of suppressing the proliferation of urinary bladder cancer cells (JB-V235 cells) was evaluated according to the same procedures as the Test Example 1 described above. The results of the proliferation suppressing activity test are shown in FIG. 8.

Figure 8:
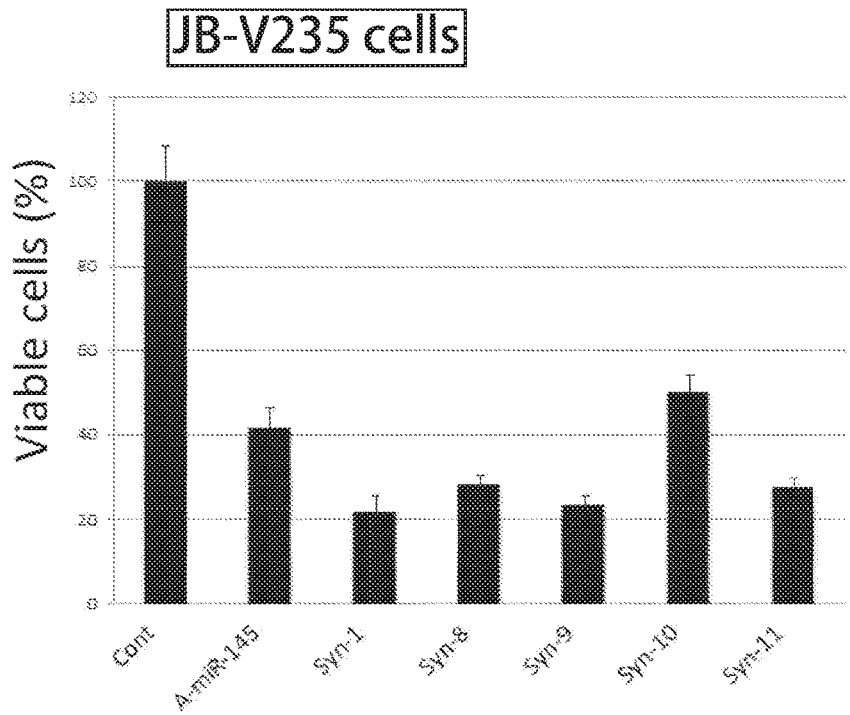
FIG. 8 shows the results of an evaluation of the viable cell count in Test Example 6.

As shown in the FIG. 8, for all of the Syn-1 and Syn-8 to Syn-11 of the present invention, the viable cell count was decreased compared to the control plot. Furthermore, in the Syn-1, Syn-8, Syn-9, and Syn-11, the viable cell count was particularly decreased, and in the Syn-1 and Syn-9, the viable cell count was more significantly decreased.

Test Example 7

Production of Unit Structure (unitPIC) Type Pharmaceutical Composition

A block copolymer was produced according to the description of the Examples of WO 2013/162041. Specifically, a block copolymer having a structure in which a hydrophilic polymer chain segment is composed of two PEG's (respectively having a molecular weight of 10 kDa), and a cationic polyamino acid segment is composed of twenty ornithine residues, was produced.

Subsequently, a double-stranded nucleic acid molecule and the block copolymer produced as described above were separately dissolved in a 10 mM HEPES buffer solution (pH 7.3), and the nucleic acid molecule and the block copolymer were mixed such that the N/P ratio (defined as [total number (N) of cationic groups in the block copolymer]/[total number (P) of phosphoric acid groups in the nucleic acid]) would be 5. Thereby, a unit structure (unit PIC) type pharmaceutical composition was produced. Here, as the double-stranded nucleic acid molecule, each of control miRNA (negative control plot (Cont); purchased from. Dharmacon, Inc.), A-miR-145, or the Syn-1, Syn-9 or Syn-12 synthesized as described above was used.

On the other hand, the same double-stranded nucleic acid molecules described above were respectively encapsulated in liposomes, and thereby, liposome type pharmaceutical compositions were produced. Specifically, a liposome type pharmaceutical composition was produced by incubating cationic liposomes and a double-stranded nucleic acid molecule in a reaction liquid.

Figure 9:
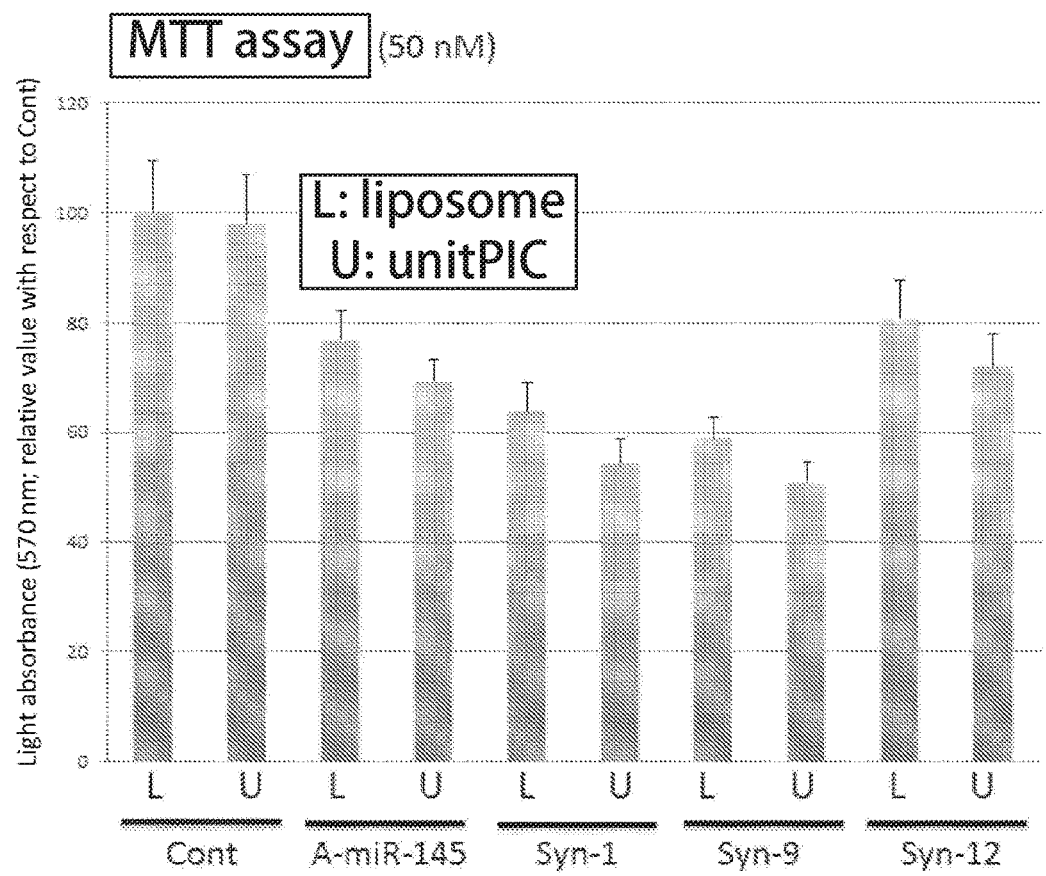
FIG. 9 shows the results of the MTT assay in Test Example 7.

An MTT assay was carried out using each of the unit structure type pharmaceutical composition and the liposome type pharmaceutical composition produced as such. Specifically, JB-V235 cells that had been subjected to three-dimensional culture were used, and the MTT assay was performed by lyzing the cells in a buffer. The results of the MTT assay are shown in FIG. 9. Meanwhile, in regard to the results shown in the FIG. 9, it is implied that as the value of light absorbance (relative value % with respect to the negative control plot (Cont)) is smaller, proliferation of the cancer cells is further suppressed.

As shown in the FIG. 9, the Syn-1 and Syn-9 of the present invention exhibited a high cancer cell proliferation suppressing effect, compared to Cont, A-miR-145, and Syn-12 (double-stranded nucleic acid molecule having a mismatch of being chemically modified). Furthermore, in both of the Syn-1 and Syn-9, the form of the unit structure (unitPIC) type pharmaceutical composition exhibited a significantly high cancer cell proliferation suppressing effect, compared to the form of the liposome type pharmaceutical composition.

This patent application is based on Japanese Patent Application No. 2016-213131, filed on Oct. 31, 2016, the entirety of which has been incorporated herein by reference.

The invention claimed is:

1. A double-stranded nucleic acid molecule e, comprising a first polynucleotide chain including a base sequence represented by the following Chemical Formula (1) (SEQ ID NO:1), and a second polynucleotide chain including a base sequence complementary to the first polynucleotide chain:

```
Chemical Formula (1):
                                        SEQ ID NO: 1
5'-AGGGA(T/U)(T/U)CC(T/U)GGGAAAAC(T/U)GGACNN-
(L-M)_k-3'
``` wherein in the Chemical Formula (1), (T/U) represents T or U; Ns each independently represent A, C, G, T, U, or a deletion; k represents 0 or 1; and L represents a substituted or unsubstituted cyclic compound-containing group represented by any one of the following Chemical Formulas (2a) to (2g):

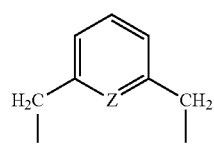

(2a)

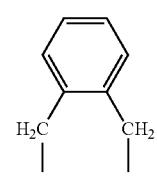

(2b)

(2c)
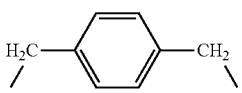

(2d)
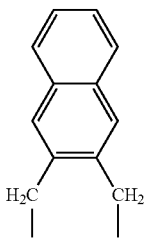

(2e)
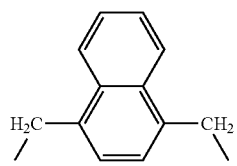

(2f)
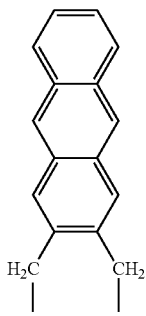

(2g)
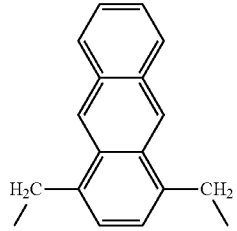

wherein in the Chemical Formula (2a), Z represents CH or N, or a divalent group in which two or more of the cyclic compound-containing groups are respectively linked through a phosphodiester bond; M represents a hydroxyl group or a —O— hydroxyl protective group; wherein the nucleotides constituting the first polynucleotide chain may be each independently substituted by a base containing a modified sugar moiety selected from the group consisting of 2'-O-methyl, 2'-methoxyethoxy, 2'-fluoro, 2'-allyl, 2'-O-[2(methylamino)-2-oxoethyl], 4'-thio, 4'-(CH$_2$)$_2$—O-2'-crosslinking, 2'-locked nucleic acid, or 2'-O—(N-methylcarbamate), and the phosphodiester bonds constituting the first polynucleotide chain may be each independently substituted with a phosphorus atom-modified bond represented by the following Chemical Formula (3):

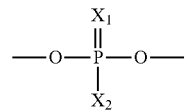
(4)

wherein in the Chemical Formula (3), $X^1$s each independently represent O, S, or Se, $X^2$s independently represent OH or O$^-$, SH or S$^-$, SeH or Se$^-$, an alkyl group having 1 to 4 carbon atoms, or a morpholino group (provided that the case where $X^1$ is O and $X^2$ is O$^-$ is excluded).

2. The double-stranded nucleic acid molecule according to claim 1, wherein
the numbers of bases of the first polynucleotide chain and the second polynucleotide chain are each independently 23 to 30 bases.

3. The double-stranded nucleic acid molecule according to claim 1, wherein
(T/U) in the base sequence set forth in the SEQ ID NO:1 is U.

4. The double-stranded nucleic acid molecule according to claim 1, wherein
NN in the base sequence set forth in the SEQ ID NO:1 is GG or TT.

5. The double-stranded nucleic acid molecule according to claim 1, wherein
the second polynucleotide chain includes a base sequence represented by the following Chemical Formula (5) (SEQ ID NO:2):

```
Chemical Formula (5):
                                    SEQ ID NO: 2
5'-GUCCAGUUUUCCCAGGAAUCCCUN'N'-(L-M)$_k$-3'
``` provided that in the Chemical Formula (5) (SEQ ID NO:2), N's each independently represent A, C, G, T, U, or a deletion; k, L, and M have the same definitions as described above; wherein, the nucleotides constituting the second polynucleotide chain may be each independently substituted by a base containing a modified sugar moiety selected from the group consisting of 2'-O-methyl, 2'-methoxyethoxy, 2'-fluoro, 2'-allyl, 2'-O-[2(methylamino)-2-oxoethyl], 4'-thio, 4'-(CH$_2$)$_2$—O-2'-crosslinking, 2'-locked nucleic acid, or 2'-O—(N-methylcarbamate), and the phosphodiester bonds constituting the second polynucleotide chain may be each independently substituted by a phosphorus atom-modified bond represented by the Chemical Formula (3).

6. The double-stranded nucleic acid molecule according to claim 5, wherein
N'N' in the base sequence set forth in the SEQ ID NO:2 is GG.

7. A vector comprising a base sequence encoding the double-stranded nucleic acid molecule according to claim 1.

8. A method for preventing and/or treating a tumor, the method comprising
administering the double-stranded nucleic acid molecule according to claim 1, to a test subject.

9. The method according to claim 8, wherein
the tumor is selected from the group consisting of urinary bladder cancer, colon cancer, breast cancer, leukemia, ovarian cancer, prostate cancer, hepatocarcinoma, lung cancer, stomach cancer, esophageal cancer, pancreatic cancer, neuroglioma, pharyngeal cancer, nasopharyngeal cancer, oral cancer, and pituitary tumor.

10. The double-stranded nucleic acid molecule according to claim 4, wherein
NN in the base sequence set forth in the SEQ ID NO:1 is GG.

11. The double-stranded nucleic acid molecule according to claim 4, wherein
the second polynucleotide chain includes a base sequence represented by the following Chemical Formula (5) (SEQ ID NO:2):

```
Chemical Formula (5):
                                      SEQ ID NO: 2
5'-GUCCAGUUUUCCCAGGAAUCCCUN'N'-(L-M)_k-3'
``` provided that in the Chemical Formula (5) (SEQ ID NO:2), N's each independently represent A, C, G, T, U, or a deletion; k, L, and M have the same definitions as described above; wherein, the nucleotides constituting the second polynucleotide chain may be each independently substituted by a base containing a modified sugar moiety selected from the group consisting of 2'-O-methyl, 2'-methoxyethoxy, 2'-fluoro, 2'-allyl, 2'-O-[2(methylamino)-2-oxoethyl], 4'-thio, 4'-(CH$_2$)$_2$—O-2'-crosslinking, 2'-locked nucleic acid, or 2'-O—(N-methylcarbamate), and the phosphodiester bonds constituting the second polynucleotide chain may be each independently substituted by a phosphorus atom-modified bond represented by the Chemical Formula (3).

12. The double-stranded nucleic acid molecule according to claim 11, wherein
N'N' in the base sequence set forth in the SEQ ID NO:2 is GG.

13. The double-stranded nucleic acid molecule according to claim 12, wherein
NN in the base sequence set forth in the SEQ ID NO:1 is GG.

14. Any one of the following double-stranded nucleic acid molecules:
a double-stranded nucleic acid molecule including a first polynucleotide chain comprising a base sequence set forth in the following SEQ ID NO:3 and a second polynucleotide chain comprising a base sequence set forth in the following SEQ ID NO:4;
a double-stranded nucleic acid molecule including a first polynucleotide chain comprising a base sequence set forth in the following SEQ ID NO:13 and a second polynucleotide chain comprising a base sequence set forth in the following SEQ ID NO:4; and
a double-stranded nucleic acid molecule including a first polynucleotide chain comprising a base sequence set forth in the following SEQ ID NO:14 and a second polynucleotide chain comprising a base sequence set forth in the following SEQ ID NO:15:

```
SEQ ID NO: 3:
5'-AGGGAUUCCUGGGAAAACUGGACGG-(L-M)_k-3'

SEQ ID NO: 4:
5'-GUCCAGUUUUCCCAGGAAUCCCUGG-(L-M)_k-3'

SEQ ID NO: 13:
5'-AGGGAUUCCUGGGAAAACUGGAC-(L-M)_k-3'
```

```
-continued
SEQ ID NO: 14:
5'-AGGGAUUCCUGGGAAAACUGGAC-(L-M)_k-3'

SEQ ID NO: 15:
5'-GUCCAGUUUUCCCAGGAAUCCCU-(L-M)_k-3'
``` wherein k represents 0 or 1; L represents a substitutes or unsubstituted cyclic compound-containing group represented by any one of the following Chemical Formulas (2a) to (2g):

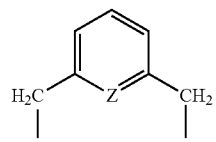

(2a)

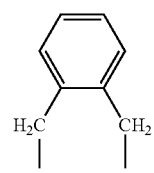

(2b)

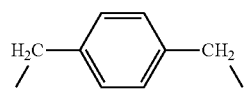

(2c)

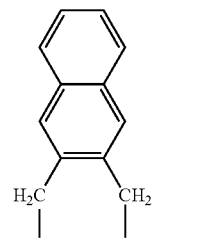

(2d)

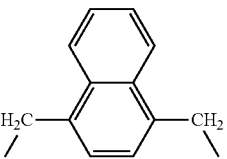

(2e)

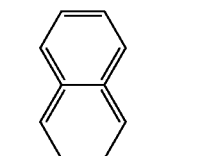

(2f)

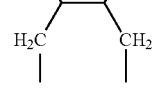

-continued (2g)

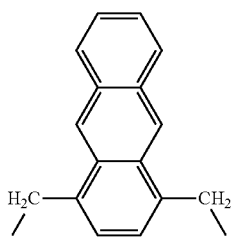

wherein in the Chemical Formula (2a), Z represents CH or N, or a divalent group having two or more of the cyclic compound-containing groups linked to each other through a phosphodiester bond; and M represents a hydroxyl group or a —O-hydroxyl protective group.

15. Any one of the following double-stranded nucleic acid molecules:
  a double-stranded nucleic acid molecule including a first polynucleotide chain comprising a base sequence set forth in the following SEQ ID NO:3 and a second polynucleotide chain comprising a base sequence set forth in the following SEQ ID NO:4;
  a double-stranded nucleic acid molecule including a first polynucleotide chain comprising a base sequence set forth in the following SEQ ID NO:13 and a second polynucleotide chain comprising a base sequence set forth in the following SEQ ID NO:4; and
  a double-stranded nucleic acid molecule including a first polynucleotide chain comprising a base sequence set forth in the following SEQ ID NO:14 and a second polynucleotide chain comprising a base sequence set forth in the following SEQ ID NO:15:

```
                                        SEQ ID NO: 3
5'-AGGGAUUCCUGGGAAAACUGGACGG

SEQ ID NO: 4
5'-GUCCAGUUUUCCCAGGAAUCCCUGG

SEQ ID NO: 13
5'-AGGGAUUCCUGGGAAAACUGGAC

SEQ ID NO: 14
5'-AGGGAUUCCUGGGAAAACUGGAC-BP

SEQ ID NO: 15
5'-GUCCAGUUUUCCCAGGAAUCCCU-BP
``` wherein BP represents a group having the following structure:

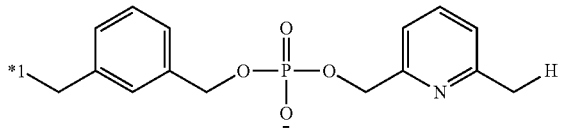

wherein *1 represents a site of bonding to an oxygen atom of a phosphodiester bond on the 3'-terminal side bonded to the base of a nucleotide at the 3'-terminal of a polynucleotide chain.

* * * * *